(12) United States Patent
Chen et al.

(10) Patent No.: US 11,615,560 B2
(45) Date of Patent: Mar. 28, 2023

(54) LEFT-ATRIAL-APPENDAGE ANNOTATION USING 3D IMAGES

(71) Applicant: EchoPixel, Inc., Santa Clara, CA (US)

(72) Inventors: Anthony Gee Young Chen, Portland, OR (US); Yu Zhang, Concord, MA (US); Jeffrey A. Kasten, San Mateo, CA (US); Sergio Aguirre-Valencia, San Jose, CA (US)

(73) Assignee: EchoPixel, Inc., Santa Clara, CA (US)

( * ) Notice: Subject to any disclaimer, the term of this patent is extended or adjusted under 35 U.S.C. 154(b) by 265 days.

(21) Appl. No.: 16/790,955

(22) Filed: Feb. 14, 2020

(65) Prior Publication Data

US 2020/0265618 A1 Aug. 20, 2020

Related U.S. Application Data

(60) Provisional application No. 62/805,961, filed on Feb. 15, 2019.

(51) Int. Cl.
*G06T 11/00* (2006.01)
*A61B 34/10* (2016.01)
(Continued)

(52) U.S. Cl.
CPC ............ *G06T 11/008* (2013.01); *A61B 34/10* (2016.02); *G16H 30/40* (2018.01); *G16H 50/50* (2018.01); *A61B 8/0883* (2013.01); *A61B 90/37* (2016.02); *A61B 2034/105* (2016.02); *G06T 2210/41* (2013.01)

(58) Field of Classification Search
CPC .... A61B 2017/00216; A61B 2034/101; A61B 2034/102; A61B 2034/105; A61B 2034/107; A61B 2034/2048; A61B 2034/2051; A61B 2034/2065; A61B 2090/364; A61B 2090/371; A61B 2090/372; A61B 34/10; A61B 34/20; A61B 6/032; A61B 6/4441; A61B 6/461; A61B 6/462; A61B 6/466; A61B 6/486; A61B 6/487; A61B 6/50; A61B 6/5205; A61B 8/0883; A61B 90/37; G06T 11/008; G06T 2210/41; G16H 15/00; G16H 30/40; G16H 40/63; G16H 50/50
See application file for complete search history.

(56) References Cited

U.S. PATENT DOCUMENTS

2017/0340336 A1* 11/2017 Osypka .................. B33Y 10/00
2019/0090951 A1* 3/2019 Camus ................... A61B 8/483

* cited by examiner

*Primary Examiner* — Manuchehr Rahmjoo
(74) *Attorney, Agent, or Firm* — Steven Stupp

(57) ABSTRACT

A computer that determines at least an anatomic feature of a left atrial appendage (LAA) is described. During operation, the computer generates a 3D image associated with an individual's heart. This 3D image may present a view along a perpendicular direction to an opening of the LAA. Then, the computer may receive information specifying a set of reference locations. For example, the set of reference locations may include: a location on a circumflex artery, a location between a superior portion of the LAA and a left pulmonary vein, and/or a location on a superior wall of the LAA and distal to trabeculae carneae. Next, the computer automatically determines, based, at least in part, on the set of reference locations, at least the anatomical feature of the LAA, which is associated with the opening of the LAA and a size of a device used in an LAA closure (LAAC) procedure.

20 Claims, 25 Drawing Sheets

(51) Int. Cl.
 *G16H 30/40* (2018.01)
 *G16H 50/50* (2018.01)
 *A61B 90/00* (2016.01)
 *A61B 8/08* (2006.01)

LAAC LANDING ZONE MEASUREMENT

[LANDING ZONE WORKFLOW] [RESET LANDING ZONE] [START EXPECTED SIZE MEASUREMENT]

PROXIMAL MEASUREMENT DISTANCE FROM CENTER
0 mm —————————————— 10 mm  3.4
CENTER        PROXIMATE

DISTAL MEASUREMENT DISTANCE FROM CENTER
0 mm —————————————— 10 mm  5.0
CENTER         DISTAL

ROTATE LANDING ZONE
[PROXIMALLY]   [DISTALLY]

SWITCH VIEW
[LANDING ZONE]
[PROXIMAL]   [CENTER]   [DISTAL]

SET VISIBILITY
[LANDING ZONE]   [LAA PLANE]
[PROXIMAL]   [CENTER]   [DISTAL]

|  | PROXIMAL | CENTER | DISTAL |
|---|---|---|---|
| DIST. TO LIMBUS (mm) | 18.3 | 21.9 | 26.8 |
| MAX. DIAMETER (mm) | 31.0 | 30.3 | 29.0 |
| MIN. DIAMETER (mm) | 23.7 | 22.8 | 21.8 |
| AREA (mm$^2$) | 568.5 | 535.7 | 480.4 |
| EQUIV. DIAMETER (mm) | 27.3 | 26.8 | 25.2 |
| MAX. LENGTH (mm) | 34.3 | 35.1 | 32.5 |
| ANGLE FROM NORMAL | 49.0 | 48.0 | 43.0 |

USER INTERFACE 1700

LEFT-ATRIAL-APPENDAGE ANNOTATION USING 3D IMAGES

CROSS REFERENCE TO RELATED APPLICATION

This application claims the benefit of U.S. Provisional Application No. 62/805,961, entitled "Left-Atrial-Appendage Annotation Using 3D Images," by Anthony Chen, et al., filed Feb. 15, 2019, the contents of which are hereby incorporated by reference.

This application is related to: U.S. patent application Ser. No. ***, "Glasses-Free Determination of Absolute Motion," filed on Feb. 8, 2019; U.S. patent application Ser. No. 16/101,416, "Multi-Point Annotation Using a Haptic Plane," filed on Aug. 11, 2018; U.S. patent application Ser. No. 16/101,417, "Multi-Point Annotation Using a Haptic Plane," filed on Aug. 11, 2018; and U.S. patent application Ser. No. 14/120,519, "Image Annotation Using a Haptic Plane," filed on May 28, 2014, the contents of each of which are herein incorporated by reference.

BACKGROUND

Field

The described embodiments relate to computer-based techniques for annotating one or more features based at least in part on computed tomography (CT) data, for using the annotation information to determine a device size and/or for determining a surgical plan.

Related Art

A left atrial appendage (LAA) is a small extension of the left atrium that can increase the chance of an embolism (and, thus, a cerebral vascular accident or a stroke) in a patient with atrial fibrillation. LAA closure (LAAC) is a procedure used to treat patients with atrial fibrillation who cannot tolerate long-term anticoagulant therapy. During LAAC, a catheter is used to insert a device into an LAA to cap the opening and to trap potential emboli before they can exit the LAA.

However, there is significant variation in the morphology of LAAs in different patients. Consequently, proper understanding of the LAA anatomy and the surrounding anatomical structures is typically important in determining a correct device size, as well as a correct device-placement orientation and a surgical plan.

Existing protocols often use a two-dimensional (2D) transesophageal-echocardiography (TEE) data to determine a patient's anatomy and the correct device size. Then, during LAAC, a combination of 2D fluoroscopy (with continuous or pulsed X-ray imaging) and 2D TEE are typically used by an invasive cardiologist to guide the placement of the device.

Unfortunately, 2D TEE usually provides limited anatomical understanding. For example, approximate anatomical dimensions are typically determined based at least in part on four different 2D TEE views or perspectives, and the results can vary based at least in part on user experience and the measurement technique. More generally, 2D projections of a 3D object (such as 2D TEE or fluoroscopy) are often difficult to interpret. Consequently, uncertainty can be added to the device sizing, the surgical plan, and the procedure itself, which can make LAAC more challenging and can adversely impact patient outcomes.

SUMMARY

In a first group of embodiments, a computer that determines at least an anatomic feature of a left atrial appendage (LAA) is described. During operation, the computer generates a 3D image (such as a 3D CT image) associated with an individual's heart. This 3D image may present a view along a perpendicular direction to an opening of the LAA. Then, the computer may receive (or access in a computer-readable memory) information specifying a set of reference locations. Next, the computer automatically determines, based, at least in part, on the set of reference locations, at least the anatomical feature of the LAA, which is associated with the opening of the LAA and a size of a device used in an LAA closure (LAAC) procedure.

For example, the set of reference locations may include: a location on a circumflex artery, a location between a superior portion of the LAA and a left pulmonary vein (such as a tip of limbus), and a location on a superior wall of the LAA and distal to trabeculae carneae.

Note that the 3D image may provide an endoluminal view of the individual's anatomy relative to a two-dimensional (2D) sectioning plane.

Moreover, the anatomical feature may include a volume, proximal and distal to a central cross-sectional area of the opening to the LAA along the perpendicular direction, in which the size of the device is unchanged. Furthermore, the anatomical feature may include one or more of: the central cross-sectional area of the opening to the LAA, a wall thickness of the LAA, a diameter extremum of the central cross-sectional area of the opening, and/or a deepest depth of the device in the LAA.

Additionally, the automatic determination may involve determining cross-sectional areas of openings to the LAA at different distal locations toward an LAA satrium, and confirming that the size of the device is unchanged at the different distal locations.

In some embodiments, the computer determines the size of the device based, at least in part, on the determined anatomical feature, and provides information specifying the determined device size. Alternatively, the computer may receive (or may access in a computer-readable memory) the size of the device. Moreover, the computer may compute a surgical plan for the LAAC procedure on the individual based, at least in part, on the size of the device, an associated predefined device geometrical model, a landing zone for successful deployment of the device, a C-arm position and an actual or a simulated fluoroscope image, and/or a septal cross-section plan. For example, the surgical plan may include navigation of the device to the LAA and an orientation of the device to occlude the LAA. Note that CT measurements can be fused or viewed superimposed over a simulated fluoroscope image.

In some embodiments, the size of the device is determined using a model of the device. For example, the model of the device may include a finite element model that describes the compliance of the device to tissue.

Furthermore, the computer may receive the information from a user. For example, the information may be received from an interaction tool. Alternatively or additionally, the information may correspond to haptic interaction between a digit of the user and a display.

Additionally, the computer may receive (or access in a computer-readable memory) information specifying a central cross-sectional area of the opening to the LAA.

Another embodiment provides a non-transitory computer-readable storage medium that stores program instructions for use with the computer. When executed by the computer, the program instructions cause the computer to perform at least some of the operations described above.

Another embodiment provides a method, which may be performed by the computer. During the method, the computer may perform at least some of the operations described above.

In a second group of embodiments, a computer may perform one or more measurements of an ostium or opening in an LAA, each of which may be perpendicular to the deepest visible point in the LAA, and one or more coordinates of a septal cross-section plan (e.g., where the septum is to be crossed in a surgical plan). Moreover, the computer may determine a route or path for how to navigate from the septum crossing to the ostium of the LAA. Alternatively or additionally, during a surgical procedure, in a first mode, a model of a device used to close an LAA may be registered to a patient's anatomy using, e.g., ultrasound (such as an echocardiogram or 2D TEE). Then, the model may be displayed, in real time, at the appropriate dynamic position and superimposed on or independently of the actual device in a 3D image and/or a simulated 2D fluoroscopy image. In some embodiments, landmarks may be displayed to assist the surgeon in the surgical procedure. Furthermore, in a second mode, the model may be removed from the 3D image and/or the simulated 2D fluoroscopy image.

Another embodiment provides a non-transitory computer-readable storage medium that stores program instructions for use with the computer. When executed by the computer, the program instructions cause the computer to perform at least some of the operations described above.

Another embodiment provides a method, which may be performed by the computer. During the method, the computer may perform at least some of the operations described above.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

FIG. 17 is a drawing illustrating a user interface in accordance with an embodiment of the present disclosure.

FIG. 23 is a drawing illustrating dynamic mapping of pixels to tracked eye positions of a viewer in accordance with an embodiment of the present disclosure.

Figure 1:
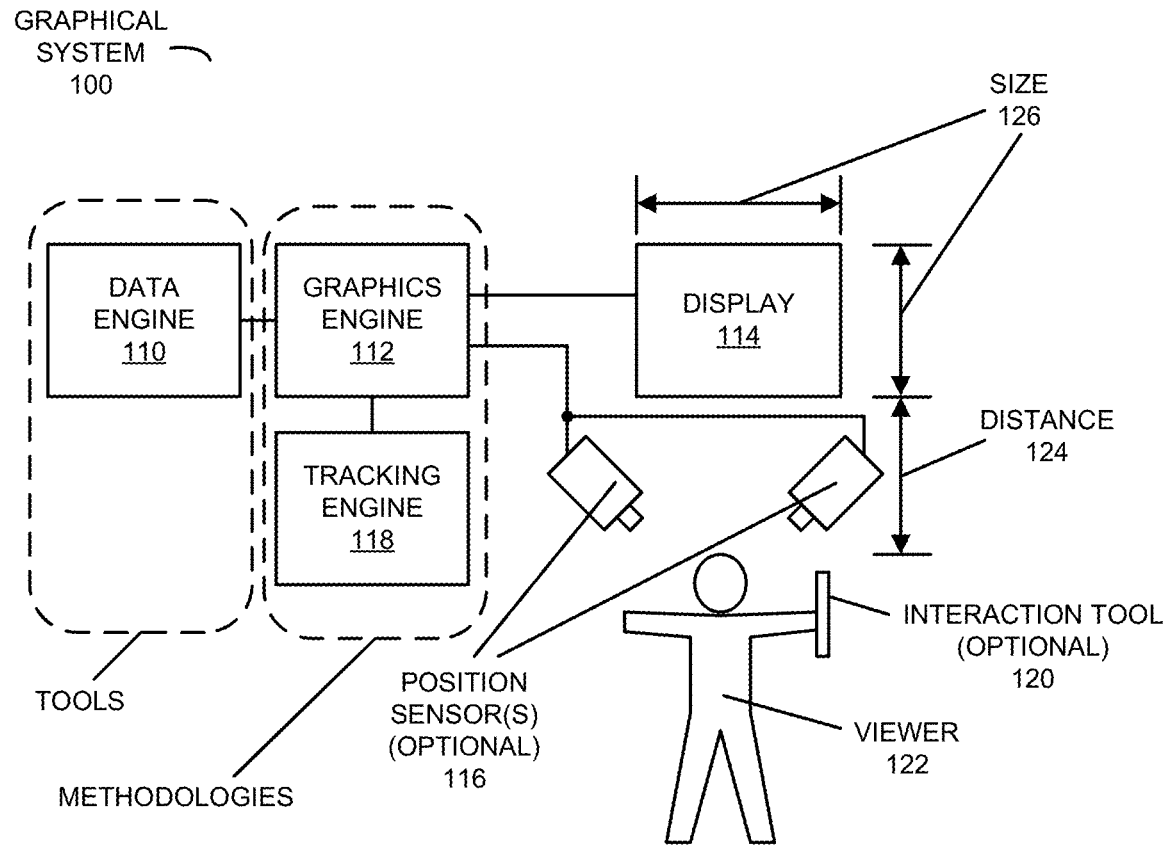
FIG. 1 is a block diagram illustrating a graphical system in accordance with an embodiment of the present disclosure.

Table 1 provides pseudo-code for a segmentation calculation at the interface between tissue classes in accordance with an embodiment of the present disclosure.

Table 2 provides a representation of a problem-solving virtual instrument in accordance with an embodiment of the present disclosure.

Note that like reference numerals refer to corresponding parts throughout the drawings. Moreover, multiple instances of the same part are designated by a common prefix separated from an instance number by a dash.

DETAILED DESCRIPTION

Human perception of information about the surrounding environment contained in visible light (which is sometimes referred to as 'eyesight,' 'sight,' or 'vision') is facilitated by multiple physiological components in the human visual system, including senses that provide sensory inputs and the cognitive interpretation of the sensory inputs by the brain. The graphical system in the present application provides rendered images that intuitively facilitate accurate human perception of 3D visual information (i.e., the awareness of an object or a scene through physical sensation of the 3D visual information). Notably, the graphical system in the present application provides so-called True 3D via rendered left-eye and right-eye images that include apparent image parallax (i.e., a difference in the position of the object or the scene depicted in the rendered left-eye and the right-eye images that approximates the difference that would occur if the object or the scene were viewed along two different lines of sight associated with the positions of the left and right eyes). This apparent image parallax may provide depth acuity (the ability to resolve depth in detail) and thereby triggers realistic stereopsis in an individual (who is sometimes referred to as a 'user,' a 'viewer' or an 'observer'), i.e., the sense of depth (and, more generally, actual 3D information) that is perceived by the individual because of retinal disparity or the difference in the left and right retinal images that occur when the object or the scene is viewed with both eyes or stereoscopically (as opposed to viewing with one eye or monoscopically).

The True 3D provided by the graphical system may incorporate a variety of additional features to enhance or maximize the depth acuity. Notably, the depth acuity may be enhanced by scaling the objects depicted in left-eye and the right-eye images prior to rendering based at least in part on the spatial resolution of the presented 3D visual information and the viewing geometry. Moreover, the graphical system may include motion parallax (the apparent relative motion of a stationary object against a background when the individual moves) in a sequence of rendered left-eye and right-eye images so that the displayed visual information is modified based at least in part on changes in the position of the individual. This capability may be facilitated by a sensor input to the graphical system that determines or indicates the motion of the individual while the individual views the rendered left-eye and the right-eye images. Furthermore, the sequence of rendered left-eye and right-eye images may include prehension, which, in this context, is the perception by the individual of taking hold, seizing, grasping or, more generally, interacting with the object. This capability may be facilitated by another sensor input to the graphical system that monitors interaction between the individual and the displayed visual information. For example, the individual may interact with the object using a stylus or their hand or finger. In addition, the depth acuity offered by the graphical system may be enhanced through the use of monoscopic depth cues, such as: relative sizes/positions (or geometric perspective), lighting, shading, occlusion, textural gradients, and/or depth cueing.

In a wide variety of applications, True 3D may allow the individual to combine cognition (i.e., a deliberative conscious mental process by which one achieves knowledge) and intuition (i.e., an unconscious mental process by which one acquires knowledge without inference or deliberative thought). This synergistic combination may further increase the individual's knowledge, allow them to use the graphical system to perform tasks more accurately and more efficiently. For example, this capability may allow a physician to synthesize the emotional function of the right brain with the analytical functions of the left brain to interpret the True 3D images as a more accurate and acceptable approximation of reality. In radiology, this may improve diagnoses or efficacy, and may increase the confidence of radiologists when making decisions. As a consequence, True 3D may allow radiologists to increase their throughput or workflow (e.g., the enhanced depth acuity may result in improved sensitivity to smaller features, thereby reducing the time needed to accurately resolve features in the rendered images). Alternatively, surgeons can use this capability to: plan surgeries or to perform virtual surgeries (for example, to rehearse a surgery), size implantable devices, and/or use live or real-time image data to work on a virtual or a real patient during a surgery (such as at a surgical table), which may otherwise be impossible using existing graphical systems. Furthermore, because the visual information in True 3D intuitively facilitates accurate human perception, it may be easier and less tiring for physicians to view the images provided by the graphical system than those provided by existing graphical systems. Collectively, these features may improve patient outcomes and may reduce the cost of providing medical care.

While the embodiments of True 3D may not result in perfect perception of the 3D visual information by all viewers (in principle, this may require additional sensory inputs, such as those related to balance), in general the deviations that occur may not be detected by most viewers. Thus, the graphical system may render images based at least in part on a volumetric virtual space that very closely approximates what the individual would see with their own visual system. As described further below in the discussion of applications of the graphical system, the deviations that do occur in the perception of the rendered images may be defined based at least in part on a given application, such as how accurately surgeons are able to deliver treatment based at least in part on the images provided by the graphical system.

Graphical System

FIG. 1 presents a block diagram of a graphical system 100, including a data engine 110, graphics (or rendering) engine 112, display 114, one or more optional position sensor(s) 116, and tracking engine 118. This graphical system may facilitate close-range stereoscopic viewing of 3D objects (such as those depicting human anatomy) with unrestricted head motion and hand-directed interaction with the 3D objects, thereby providing a rich holographic experience.

During operation, data engine 110 may receive input data (such as a computed-tomography or CT scan, histology, an ultrasound image, a magnetic resonance imaging or MRI scan, or another type of 2D image slice depicting volumetric information), including dimensions and spatial resolution. In an exemplary embodiment, the input data may include representations of human anatomy, such as input data that is compatible with a Digital Imaging and Communications in Medicine (DICOM) standard. However, a wide variety of types of input data may be used (including non-medical data), which may be obtained using different imaging techniques, different wavelengths of light (microwave, infrared, optical, X-ray), etc.

After receiving the input data, data engine 110 may: define segments in the data (such as labeling tissue versus air); other parameters (such as transfer functions for voxels); identify landmarks or reference objects in the data (such as anatomical features); and identify 3D objects in the data (such as the lung, liver, colon and, more generally, groups of voxels). One or more of these operations may be performed by or may be augmented based at least in part on input from a user or viewer 122 of graphical system 100.

As described further below, based at least in part on the information output by data engine 110 (including the left and right eye coordinates and distance 124 of viewer 122 from display 114), graphics engine 112 may define, for the identified 3D objects, model matrices (which specify where the objects are in space relative to viewer 122 using a model for each of the objects), view matrices (which specify, relative to a tracking camera or image sensor in display 114 (such as a CCD or a CMOS image sensor), the location and/or gaze direction of the eyes of viewer 122), and projection or frustum matrices (which specify what is visible to the eyes of viewer 122). These model, view and frustum matrices may be used by graphics engine 112 to render images of the 3D objects. For a given eye, the rendered image may provide a 2.5D monoscopic projection view on display 114. By sequentially or spatially displaying left-eye and right-eye images that include image parallax (i.e., stereoscopic images), 3D information may be presented on display 114. These images may be appropriately scaled or sized so that the images match the physical parameters of the viewing geometry (including the position of viewer 122 and size 126 of the display 114). This may facilitate the holographic effect for viewer 122. In addition, the left-eye and the right-eye images may be displayed at a monoscopic frequency of at least 30 Hz. Note that this frequency may be large enough to avoid flicker even in ambient lighting and may be sufficient for viewer 122 to fuse the images to perceive stereopsis and motion.

Moreover, the one or more optional position sensors 116 (which may be separate from or integrated into display 114, and which may be spatially offset from each other) may dynamically track movement of the head or eyes of viewer 122 with up to six degrees of freedom, and this head-tracking (or eye-tracking) information (e.g., the positions of the eyes of viewer 122 relative to display 114) may be used by graphics engine 112 to update the view and frustum matrices and, thus, the rendered left-eye and right-eye images. In this way, the rendered images may be optimal from the viewer perspective and may include motion parallax. In some embodiments, the one or more optional position sensor(s) 116 optionally dynamically track the gaze direction of viewer 122 (such as where viewer 122 is looking). By tracking where viewer 122 is looking, graphics engine 112 may include foveated imaging when rendering images, which can provide additional depth perception. For example, the transfer functions defined by data engine 110 may be used to modify the rendering of voxels in a 3D image (such as the transparency of the voxels) based at least in part on the focal plane of viewer 122.

Furthermore, tracking engine 118 may dynamically track 3D interaction of viewer 122 with a hand or finger of viewer 122, or an optional physical interaction tool 120 (such as a stylus, a mouse or a touch pad that viewer 122 uses to interact with one or more of the displayed 3D objects), with up to six degrees of freedom. For example, viewer 122 can grasp an object and interact with it using their hand, finger and/or optional interaction tool 120. The detected interaction information provided by tracking engine 118 may be used by graphics engine 112 to update the view and frustum matrices and, thus, the rendered left-eye and right-eye images. In this way, the rendered images may update the perspective based at least in part on interaction of viewer 122 with one or more of the displayed 3D objects using their hand, finger and/or the interaction tool (and, thus, may provide prehension), which may facilitate hand-eye coordination of viewer 122.

Alternatively or additionally, tracking engine 118 may use one or more images captured by the one or more optional position sensors 116 to determine absolute motion of viewer 122 based at least in part on an anatomical feature having a predefined or predetermined size to determine absolute motion of viewer 122 along a direction between viewer 122 and, e.g., display 114. For example, the anatomical feature may be an interpupillary distance (ipd), such as the ipd associated with viewer 122 or a group of individuals (in which case the ipd may be an average or mean ipd). More generally, the anatomical feature may include another anatomical feature having the predefined or predetermined size or dimension for viewer 122 or the group of individuals. In some embodiments, the offset positions of and/or a spacing 128 between the one or more optional position sensors 116 are predefined or predetermined, which allows the absolute motion in a plane perpendicular to the direction to be determined. For example, based at least in part on angular information (such as the angle to an object in one or more images, e.g., the viewer's pupils or eyes), the positions of the one or more optional position sensors 116 (such as image sensors) and the absolute distance between a viewer 122 and a display, the absolute motion in the plane perpendicular to the direction may be determined. Consequently, using the anatomical feature as a reference and the offset positions of the one or more optional position sensors 116, tracking engine 118 can determine absolute motion of viewer 122 in 3D. By dynamically tracking the absolute motion of viewer 122, tracking engine 118 may allow viewer 122 to have quantitative virtual haptic interaction with one or more of the displayed 3D objects. As with optional interaction tool 120, the detected interaction information provided by tracking engine 118 may be used by graphics engine 112 to update the view and frustum matrices and, thus, the rendered left-eye and right-eye images. In this way, the rendered images may update the perspective based at least in part on interaction of viewer 122 with one or more of the displayed 3D objects using, e.g., motion of one or more digits, a hand and/or an arm (and, thus, may provide prehension), which may facilitate hand-eye coordination of viewer 122.

By using image parallax, motion parallax and prehension, graphical system 100 may provide cues that the human brain uses to understand the 3D world. Notably, the image parallax triggers stereopsis, while the motion parallax can enable the viewer to fuse stereoscopic images with greater depth. In addition, the kinesthetic (sensory) input associated with the prehension in conjunction with the stereopsis may provide an intuitive feedback loop between the mind, eyes and hand of viewer 122 (i.e., the rich holographic experience).

Note that the one or more optional position sensors 116 may use a wide variety of techniques to track the locations of the eyes of viewer 122 and/or where viewer 122 is looking (such as a general direction relative to display 114). For example, viewer 122 may be provided glasses with reflecting surfaces (such as five reflecting surfaces), and infrared light reflected off of these surfaces may be captured by cameras or image sensors (which may be integrated into or included in display 114). This may allow the 3D coordinates of the reflecting surfaces to be determined. In turn, these 3D coordinates may specify the location and/or the viewing direction of the eyes of viewer 122, and can be used to track head movement. However, in some embodiments the ability to determine the absolute motion using the images captured using the one or more optional position sensors 116 and based at least in part on the anatomical feature may eliminate the need for viewer 122 to wear special glasses when using graphical system 100, such as glasses having the reflecting surfaces or glasses with a known or predefined ipd. Alternatively or additionally, stereoscopic triangulation may be used, such as Leap (from Leap Motion, Inc. of San Francisco, Calif.). For example, two (left/right) camera views of the face of viewer 122 may be used to estimate what viewer 122 is looking at. Notably, image processing of at least two camera views or images may allow the 3D coordinates of the eyes of viewer 122 to be determined. Another technique for tracking head motion may include sensors (such as magnetic sensors) in the glasses that allow the position of the glasses to be tracked. More generally, a gyroscope, electromagnetic tracking (such as that offered by Northern Digital, Inc. of Ontario, Canada), a local positioning system and/or a time of flight technique may be used to track the head position of viewer 122, such as Kinect (from Microsoft Corporation of Redmond, Wash.). images and/or in a plane perpendicular to the direction In the discussion that follows, cameras or image sensors in display 114 are used as an illustrative example of a technique for tracking the location and/or gaze direction of the eyes of viewer 122.

Furthermore, instead of or in additional to optional physical interaction tool 120, in some embodiments viewer 122 may interact with displayed objects by using gestures in space (such as by moving one or more fingers on one or more of their hands). For example, a time of flight technique may be used (such as Kinect) and/or stereoscopic triangulation may be used (such as Leap). More generally, the position or motion of optional physical interaction tool 120 may be determined: optically, using magnetic sensors, using electromagnetic tracking, using a gyroscope, using stereoscopic triangulation and/or using a local positioning system.

Note that optional physical interaction tool 120 may provide improved accuracy and/or spatial control for viewer 122 (such as a surgeon) when interacting with the displayed objects.

Additionally, a wide variety of displays and display technologies may be used for display 114. In an exemplary embodiment, display 114 integrates the one or more optional position sensors 116. For example, display 114 may be provided by Infinite Z, Inc. (of Mountain View, Calif.) or Leonar3do International, Inc. (of Herceghalom, Hungary). Display 114 may include: a cathode ray tube, a liquid crystal display, a plasma display, a projection display, a holographic display, an organic light-emitting-diode display, an electronic paper display, a ferroelectric liquid display, a flexible display, a head-mounted display, a retinal scan display, and/or another type of display. In an exemplary embodiment, display 114 is a 2D display. However, in embodiments where display includes a holographic display, instead of sequentially (and alternately) displaying left-eye and right-eye images, at a given time a given pair of images (left-eye and right-eye) may concurrently displayed by display 114 or the information in the given pair of images may be concurrently displayed by display 114. Thus, display 114 may be able to display magnitude and/or phase information.

Image Processing and Rendering Operations

Graphics engine 112 may implement a vertex-graphics-rendering process in which 3D vertices define the corners or intersections of voxels and, more generally, geometric shapes in the input data. In an exemplary embodiment, graphics engine 112 uses a right-handed coordinate system. Graphics engine 112 may use physical inputs (such as the position of the eyes of viewer 122) and predefined parameters (such as those describing size 126 of display 114 in FIG. 1 and the viewing geometry) to define the virtual space based at least in part on matrices. Note that graphics engine 112 'returns' to the physical space when the left-eye and right-eye images are rendered based at least in part on the matrices in the virtual space.

In the virtual space, 3D objects may each be represented by a 4×4 matrix with an origin position, a scale and an orientation. These objects may depict images, 3D volumes, 3D surfaces, meshes, lines or points in the input data. For computational simplicity, all the vertices may be treated as three-dimensional homogeneous vertices that include four coordinates, three geometric coordinates (x, y, and z) and a scale w. These four coordinates may define a 4×1 column vector $(x, y, z, w)^T$. Note that: if w equals one, then the vector (x, y, z, 1) is a position in space; if w equals zero, then the vector (x, y, z, 0) is a position in a direction; and if w is greater than zero, then the homogeneous vertex $(x, y, z, w)^T$ corresponds to the 3D point $(x/w, y/w, z/w)^T$.

Using homogeneous coordinates, a vertex array can represent a 3D object. Notably, an object matrix M may initially be represented as $$\begin{bmatrix} m0 & m4 & m8 & m12 \\ m1 & m5 & m9 & m13 \\ m2 & m6 & m10 & m14 \\ m3 & m7 & m11 & m15 \end{bmatrix},$$

where, by default, (m0, m1, m2) may be the +x axis (left) vector (1, 0, 0), (m4, m5, m6) may be the +y axis (up) vector (0, 1, 0), (m8, m9, m10) may be the +z axis (forward) vector (0, 0, 1), m3, m7, and m11 may define the relative scale of these vectors along these axes, m12, m13, m14 specify the position of a camera or an image sensor that tracks the positions of the eyes of viewer 122, and m15 may be one.

By applying a rotation operation (R), a translation operation (T) and a scaling operation (S) across the vertex array of an object (i.e., to all of its (x, y, z, w) vectors), the object can be modified in the virtual space. For example, these operations may be used to change the position of the object based at least in part on where viewer 122 is looking, and to modify the dimensions or scale of the object so that the size and proportions of the object are accurate. Notably, a transformed vector may be determined using $$S \cdot R \cdot T \cdot I_0,$$

where $I_0$ is an initial vector in the virtual space. Note that, in a right-handed coordinate system, a rotation a about the x axis (Rx), a rotation a about the y axis (Ry) and a rotation a about the z axis (Rz), respectively, can be represented as $$Rx = \begin{bmatrix} 1 & 0 & 0 & 0 \\ 0 & \cos(a) & -\sin(a) & 0 \\ 0 & \sin(a) & \cos(a) & 0 \\ 0 & 0 & 0 & 1 \end{bmatrix},$$

$$Ry = \begin{bmatrix} \cos(a) & 0 & \sin(a) & 0 \\ 0 & 1 & 0 & 0 \\ -\sin(a) & 0 & \cos(a) & 0 \\ 0 & 0 & 0 & 1 \end{bmatrix}$$

and $$Rz = \begin{bmatrix} \cos(a) & -\sin(a) & 0 & 0 \\ \sin(a) & \cos(a) & 0 & 0 \\ 0 & 0 & 1 & 0 \\ 0 & 0 & 0 & 1 \end{bmatrix}.$$

Similarly, a translation by (x, y, z) can be represented as $$T = \begin{bmatrix} 1 & 0 & 0 & x \\ 0 & 1 & 0 & y \\ 0 & 0 & 1 & z \\ 0 & 0 & 0 & 1 \end{bmatrix},$$

a non-uniform scaling by $s_x$ along the x axis, $s_y$ along the y axis and $s_z$ along the z axis can be represented as $$S = \begin{bmatrix} s_x & 0 & 0 & 0 \\ 0 & s_y & 0 & 0 \\ 0 & 0 & s_z & 0 \\ 0 & 0 & 0 & 1 \end{bmatrix}$$

and a uniform scaling s can be represented as $$S = \begin{bmatrix} 1 & 0 & 0 & 0 \\ 0 & 1 & 0 & 0 \\ 0 & 0 & 1 & 0 \\ 0 & 0 & 0 & s \end{bmatrix}.$$

Moreover, note that an arbitrary combination of rotation, translation and scaling matrices is sometimes referred to as a 'transformation matrix' Tf. Therefore, after applying the rotation, translation and scaling matrices, the model matrix M may become a model transformation matrix Mt. This transformation matrix may include the position of the object (bx, ty, tz, 1)$^T$, the scale s of the object and/or the direction R of the object [(r1, r2, r3)$^T$, (r4, r5, r6)$^T$, (r7, r8, r9)$^T$]. Thus, the transformation matrix Mt may be generated by: translating the object to its origin position (tx, ty, tz, 1)$^T$; rotating the object by R; and/or scaling the object by s. For example, with uniform scaling the transformation matrix Mt may be represented as $$\begin{bmatrix} r1 & r4 & r7 & tx \\ r2 & r5 & r8 & ty \\ r3 & r6 & r9 & tz \\ 0 & 0 & 0 & s \end{bmatrix}.$$

In addition to the model matrices for the objects, graphics engine 112 may also implement so-called 'views' and 'perspective projections,' which may each be represented using homogeneous 4×4 matrices. The view may specify the position and/or viewing target (or gaze direction) of viewer 122 (and, thus, may specify where the objects are in space relative to viewer 122). In the virtual space, a given view matrix V (for the left eye or the right eye) may be based at least in part on the position of a camera or an image sensor that tracks the positions of the eyes of viewer 122, the location the camera is targeting, and the direction of the unit vectors (i.e., which way is up), for example, using a right-hand coordinate system. In the physical space, the view matrices V may be further based at least in part on the eye positions of viewer 122, the direction of the unit vectors and/or where viewer 122 is looking. In an exemplary embodiment, the view matrices V are created by specifying the position of the camera and the eyes of viewer 122, specifying the target coordinate of the camera and the target coordinate of the eyes of viewer 122, and a vector specifying the normalized +y axis (which may be the 'up' direction in a right-handed coordinate system). For example, the target coordinate may be the location that the camera (or the eyes of viewer 122) is pointed, such as the center of display 114.

In an exemplary embodiment, the given view matrix V is determined by constructing a rotation matrix Rv. In this rotation matrix, the 'z axis' may be defined as the normal from given camera position (px, py, pz)$^T$ minus the target position, i.e., $(z1,z2,z3)^T = \text{normal}[(px,py,pz)^T - (tx,ty,tz)^T]$.

Then, the 'x axis' may be calculated as the normal of the cross product of the 'z axis' and normalized +y axis (which may represent the 'up' direction), i.e., $(x1,x2,x3)^T = \text{normal}[\text{crosss}[(z1,z2,z3)^T, (ux,uy,uz)^T]]$.

Moreover, the un-normalized y axis may be calculated as the cross product of the 'z axis' and 'x axis,' i.e., $(y1,y2,y3)^T = \text{normal}[(z1,z2,z3)^T (x1,x2,x3)^T]$.

Thus, the complete 4×4 rotation matrix Rv for use in determining the given view matrix may be $$\begin{bmatrix} x1 & y1 & z1 & 0 \\ x2 & y2 & z2 & 0 \\ x3 & y3 & z3 & 0 \\ 0 & 0 & 0 & 1 \end{bmatrix}.$$

Next, the given view matrix V may also be determined by constructing a translation matrix Tv based at least in part on the position of one of the eyes of viewer 122 (tx, ty, tz). Notably, the translation matrix Tv may be represented as $$Tv = \begin{bmatrix} 1 & 0 & 0 & tx \\ 0 & 1 & 0 & ty \\ 0 & 0 & 1 & tz \\ 0 & 0 & 0 & 1 \end{bmatrix}.$$

Using the rotation matrix Rv and the translation matrix Tv, the inverse of the given view matrix $V^{-1}$ may be determined as $$V^{-1} = Rv \cdot Tv$$

or $$V^{-1} = \begin{bmatrix} x1 & y1 & z1 & tx \\ x2 & y2 & z2 & ty \\ x3 & y3 & z3 & tz \\ 0 & 0 & 0 & 1 \end{bmatrix}.$$

The perspective projection may use left-eye and right-eye frustums F to define how the view volume is projected on to a 2-dimensional (2D) plane (e.g., the viewing plane, such as display 114) and on to the eyes of viewer 122 (which may specify what is visible to the eyes of viewer 122). In the virtual space, a given frustum (for the left eye or the right eye) may be the portion of the 3D space (and the 3D objects it contains) that may appear or be projected as 2D left-eye or right-eye images on display 114. In the physical space, the given frustum may be the viewing volume that defines how the 3D objects are projected on to one of the eyes of viewer 122 to produce retinal images of the 3D objects that will be perceived (i.e., the given frustum specifies what one of the eyes of viewer 122 sees or observes when viewing display 114). Note that the perspective projection may project all points into a single point (an eye of viewer 122). As a consequence, the two perspective projections, one for the left eye of the viewer and another for the right eye of the viewer, are respectively used by graphics engine 112 when determining the left-eye image and the right-eye image. In general, for an arbitrary head position of viewer 122, the projection matrices or frustums for the left eye and the right eye are different from each other and are asymmetric.

Figure 2:
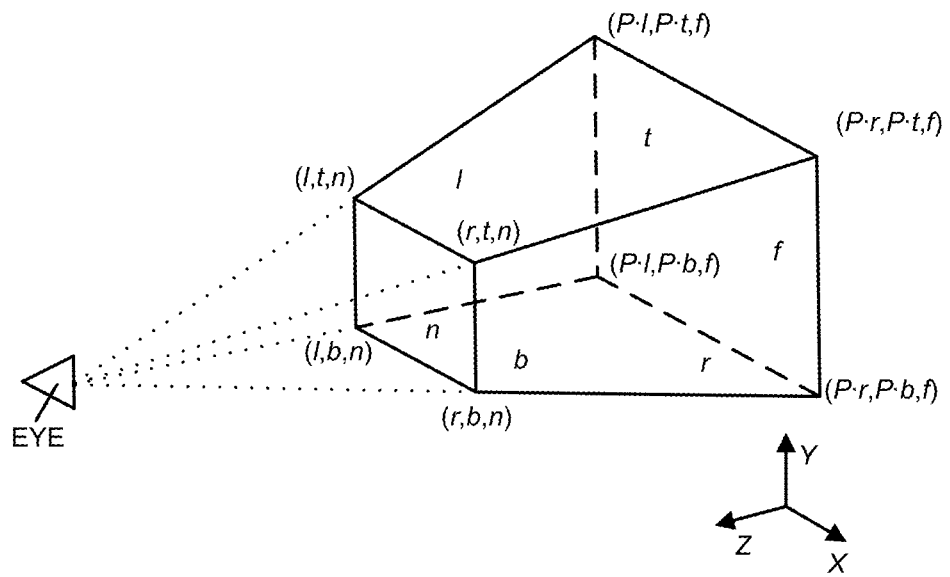
FIG. 2 is a drawing illustrating a frustum for a vertical display in the graphical system of FIG. 1 in accordance with an embodiment of the present disclosure.

FIG. 2 presents a drawing illustrating a frustum 200 for a vertical display in graphical system 100. This frustum includes: a near plane (or surface), a far (or back) plane, a left plane, a right plane, a top plane and a bottom plane. In this example, the near plane is defined at z equal to n. Moreover, the vertices of the near plane are at x equal to l and r (for, respectively, the left and right planes) and y equal to t and b (for, respectively, the top and bottom planes). The vertices of the far f plane can be calculated based at least in part on the ratio of similar triangles as $$\frac{f}{n} = \frac{\text{left}_{far}}{l} = \frac{l_{far}}{l},$$

which can be re-arranged as $$l_{far} = \left(\frac{f}{n}\right) \cdot l.$$

By defining a perspective projection factor P as $$\frac{f}{n}$$

this can be re-expressed as $$l_{far} = P \cdot l.$$

As shown in FIG. 2, the coordinates of the vertices at the far plane in frustum 200 can be expressed in terms of the coordinates at the near plane and the perspective projection factor P. Moreover, frustum (F) 200 can be expressed as a 4×4 matrix $$F = \begin{bmatrix} \frac{2n}{r-l} & 0 & \frac{r+l}{r-l} & 0 \\ 0 & \frac{2n}{t-b} & \frac{t+b}{t-b} & 0 \\ 0 & 0 & \frac{-(f+n)}{f-n} & \frac{-2fn}{f-n} \\ 0 & 0 & -1 & 0 \end{bmatrix}.$$

In an exemplary embodiment, when the head position of viewer 122 in FIG. 1 is not tracked (i.e., when motion parallax is not included), the near plane may be coincident with display 114 in FIG. 1. (In the discussion that follows, the plane of display 114 in FIG. 1 is sometimes referred to as the 'viewing plane.') In this case, frustum 200 extends behind the plane of display 114 (FIG. 1). Because viewer perception of stereopsis is high between 15 and 65 cm, and eventually decays at larger distances away from viewer 122 (FIG. 1), the far plane may define a practical limit to the number of vertices that are computed by graphics engine 112 (FIG. 1). For example, fmay be twice n. In addition, as described further below, by defining a finite space, the left-eye and right-eye images may be scaled to enhance or maximize the depth acuity resolved by viewer 122 (FIG. 1) for a given spatial resolution in the input data and the viewing geometry in graphical system 100 in FIG. 1 (which is sometimes referred to as 'stereopsis scaling' or 'stereoacuity scaling').

Figure 3:
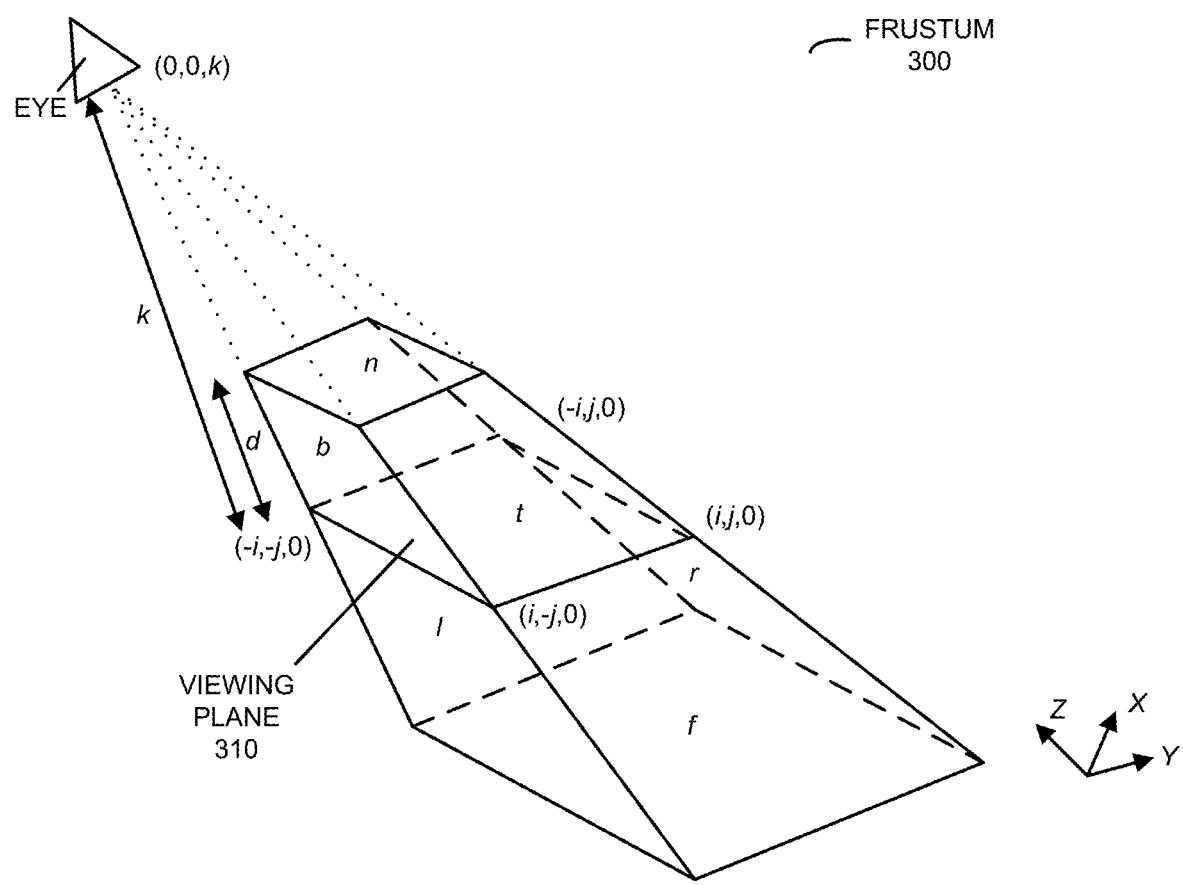
FIG. 3 is a drawing illustrating a frustum for a horizontal display in the graphical system of FIG. 1 in accordance with an embodiment of the present disclosure.
Figure 4:
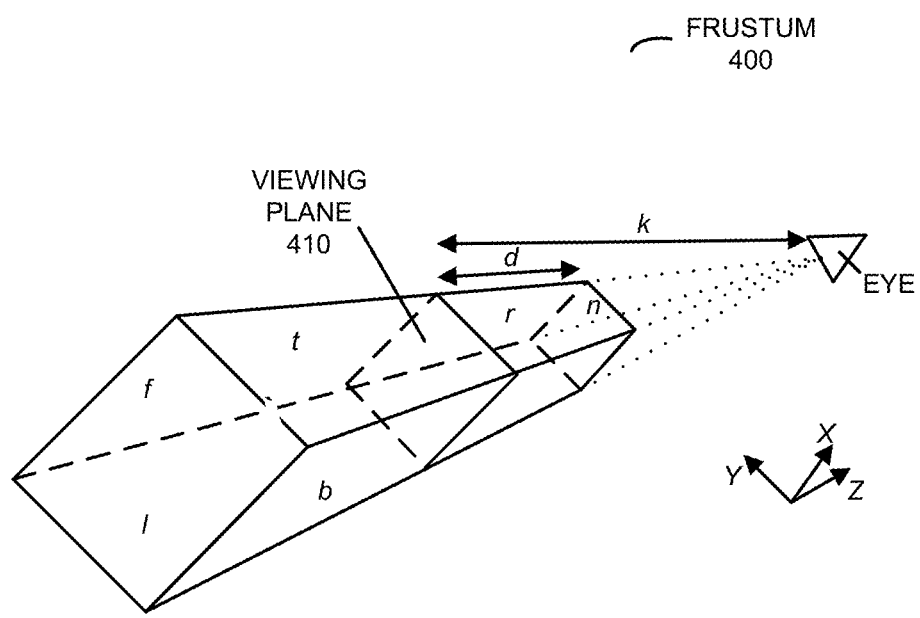
FIG. 4 is a drawing illustrating a frustum for an inclined display in the graphical system of FIG. 1 in accordance with an embodiment of the present disclosure.

While the preceding example of the frustum used a vertical display, in other embodiments display 114 (FIG. 1) may be horizontal or may be at an incline. For example, in surgical applications, display 114 (FIG. 1) may be placed on the floor. As shown in FIGS. 3 and 4, which present drawings illustrating frustums 300 (FIG. 3) and 400, in these configurations the frustums are rotated.

When the position of the head or the eyes of viewer 122 (FIG. 1) are tracked in graphical system 100 in FIG. 1 (so that the rendered left-eye and right-eye images can be modified accordingly), the viewing plane may be placed approximately in the middle of the frustums to provide back-and-forth spatial margin. This is illustrated by viewing planes 310 (FIG. 3) and 410. Moreover, as shown in FIG. 3, the coordinates of the vertices of viewing plane 310 may be left (−i), right (+i), top (+j), bottom (−j), and the z (depth) coordinate may be zero so that the near plane is at z coordinate d and the eyes of viewer 122 (FIG. 1) are at z coordinate k. (In some embodiments, the near plane is defined at the same z coordinate as the eyes of viewer 122 in FIG. 1.) Based at least in part on these coordinates, the far-plane coordinates can be determined using the perspective projection factor P.

Note that, while the preceding example defined the frustum based at least in part on the distance z from viewer 122 (FIG. 1) to display 114 (FIG. 1), in embodiments where the one or more optional position sensors 116 (FIG. 1) track the gaze direction of viewer 122 (FIG. 1), the frustum may be based at least in part on the focal point of viewer (FIG. 1). Furthermore, while a viewing plane was used as a reference in the preceding discussion, in some embodiments multiple local planes (such as a set of tiled planes) at different distances z from viewer 122 (FIG. 1) to display 114 (FIG. 1) are used.

By multiplying the left-eye (or right-eye) frustum F by the corresponding left-eye (or right-eye) view matrix V and the model transformation matrix Mt, a 2D projection in the viewing plane of a 3D object can be determined for rendering as a given left-eye (or right-eye) image. These operations may be repeated for the other image to provide stereoscopic viewing. As described further below with reference to FIG. 6, note that when rendering these 2D projections, a surface may be extracted for a collection of voxels or a volume rending may be made based at least in part on ray tracing.

In order to enhance or maximize the depth acuity resolved by viewer 122 in FIG. 1 (and, thus, to provide high-resolution depth perception), the graphics engine 112 (FIG. 1) may ensure that the geometric disparity between the left-eye and the right-eye images remains between a minimum value that viewer 122 (FIG. 1) can perceive (which is computed below) and a maximum value (beyond which the human mind merges the left-eye and the right-eye images and stereopsis is not perceived). In principle, graphics engine 112 (FIG. 1) may scale the objects in the image(s) presented to viewer 122 (FIG. 1) in proportion to their focal distance z (which is sometimes referred to as a 'geometric perspective'), or may have free control of the focal distance of viewer 122 (FIG. 1) in order to accommodate all the objects viewer 122 (FIG. 1) wants to observe. The latter option is what happens in the real world. For example, when an individual focuses on a desk and, thus, has accommodated to a short focal distance, he or she can resolve depth with a precision of around 1 mm. However, when the individual is outside and accommodates to a longer focal distance, he or she can resolve depth with a precision of around 8 cm.

In practice, because graphical system 100 (FIG. 1) implements stereoscopic viewing (which provides depth information), it is not necessary to implement geometric perspective (although, in some embodiments, geometric perspective is used in graphical system 100 in FIG. 1 addition to image parallax). Instead, in graphical system 100 (FIG. 1) objects may be scaled in proportion to the distance z of viewer 122 (FIG. 1) from display 114 (FIG. 1). As described previously, a range of distances z may occur and, based at least in part on the head-tracking information, this range may be used to create the frustum. Notably, after determining the 2D projection, graphics engine 112 (FIG. 1) may scale a given object in the image(s) presented to the viewer based at least in part on based at least in part on the viewing geometry (including the distance z) and a given spatial resolution in the input data (such as the voxel spacing, the discrete spacing between image slices, and/or, more generally, the discrete spatial sampling in the input data) in order to enhance (and, ideally, to maximize or optimize) the depth acuity. This stereopsis scaling may allow viewer 122 (FIG. 1) to perceive depth information in the left-eye and the right-eye images more readily, and in less time and with less effort (or eye strain) for discretely sampled data. As such, the stereopsis scaling may significantly improve the viewer experience and may improve the ability of viewer 122 (FIG. 1) to perceive 3D information when viewing the left-eye and the right-eye images provided by graphical system 100 (FIG. 1).

Note that the stereopsis scaling may not be typically performed in computer-aided design systems because these approaches are often model-based which allows the resulting images to readily incorporate geometric perspective for an arbitrary-sized display. In addition, stereopsis scaling is typically not performed in 2.5D graphical systems because these approaches often include markers having a predefined size in the resulting images as comparative references.

Figure 5:
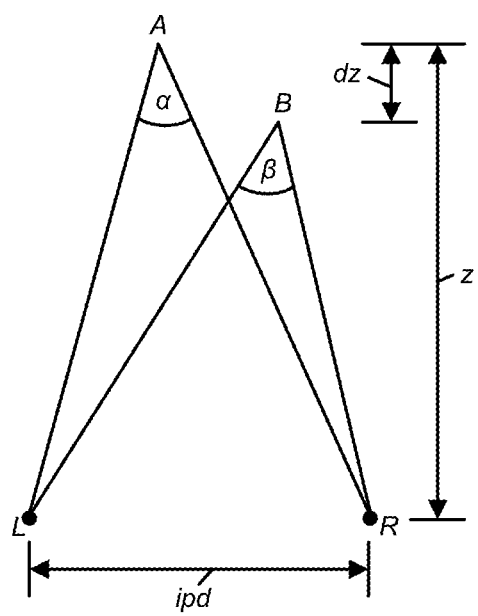
FIG. 5 is a drawing illustrating calculation of stereopsis scaling in the graphical system of FIG. 1 in accordance with an embodiment of the present disclosure.

FIG. 5 presents a drawing illustrating the calculation of the stereopsis scaling for a given spatial resolution in the input data and a given viewing geometry. In this drawing, ipd is the interpupillary distance, z is the distance to the focal point of viewer 122 (FIG. 1) (which, as noted previously, may be replaced by the distance between viewer 122 and display 114 in FIG. 1 in embodiments where the head position of viewer 122 is tracked), dz is the delta in the z (depth) position of an object to the focal point, L is the left eye-position and R is the right-eye position. Moreover, the geometric disparity $\delta_\gamma$ may be defined based at least in part on the difference in the angles α and β times L, i.e., $$\delta\gamma = L \cdot (\alpha - \beta).$$

This can be re-expressed as $$\delta\gamma = \frac{(ipd) \cdot (dz)}{z^2 + z \cdot (dz)}.$$

If z is 400 mm, the ipd is 65 mm (on average) and dz is 1 mm, the geometric disparity $\delta_\gamma$ equals $4.052 \times 10^{-4}$ radians or 82.506 arcseconds. As noted previously, viewers have minimum and maximum values of the geometric disparity $\delta\gamma$ that they can perceive. For a given distance z (which, as noted previously, may be determined by tracking the head position of viewer 122 in FIG. 1), the scale of the objects in the left-eye image and the right-eye image can be selected to enhance or maximize the depth acuity based at least in part on $$dz = \frac{\delta\gamma \cdot (z^2)}{ipd}, \tag{1}$$

which defines the minimum dz needed for stereopsis. For example, in the case of medical images, dz may be the voxel spacing. (Note that, for an x spacing dx, a y spacing dy and a z spacing dz, the voxel size dv may be defined as $$dv^2 = dx^2 + dy^2 + dz^2)$$

Moreover, the minimum value of the geometric disparity $\delta\gamma$ (which triggers stereopsis and defines the depth acuity) may be 2-10 arcseconds (which, for 10 arcseconds, is $4.486 \times 10^{-5}$ radians) and the maximum value may be 600 arcseconds (which, for 100 arcseconds, is $4.486 \times 10^{-4}$ radians). If the average distance z from the viewer to display 114 (FIG. 1) is 0.5 m (an extremum of the 0.5-1.5 m range over which the depth acuity is a linear function of distance z), the ipd equals 65 mm and the minimum value of the geometric disparity $\delta\gamma$ is 10 arcseconds, the minimum $dz_{min}$ in Eqn. 1 to maintain optimal depth acuity is 0.186 mm. Similarly, if the average distance z is 0.5 m, the ipd equals 65 mm and the maximum value of the geometric disparity $\delta\gamma$ is 100 arcseconds, the maximum $dz_{max}$ in Eqn. 1 to maintain optimal depth acuity is 1.86 mm. Defining the minimum scale $s_{min}$ as $$s_{min} = \frac{dz_{min}}{dv}$$

and the maximum scale $s_{max}$ as $$s_{max} = \frac{dz_{max}}{dv},$$

and for an isometric 1 mm voxel resolution, the minimum scale $s_{min}$ is 0.186 and the maximum scale $s_{max}$ is 1.86. Therefore, in this example the objects in left-eye and the right-eye images can be scaled by a factor between 0.186 and 1.86 (depending on the average tracked distance z) to optimize the depth acuity. Note that, in embodiments where the one or more optional position sensors 116 (FIG. 1) track the gaze direction of viewer 122 (FIG. 1), the stereopsis scaling may be varied based at least in part on the focal point of viewer 122 (FIG. 1) instead of the distance z from viewer 122 (FIG. 1) to display 114 (FIG. 1).

While the preceding example illustrated the stereopsis scaling based at least in part on an average $\delta\gamma$ and an average ipd, in some embodiments the stereopsis scaling is based at least in part on an individual's $\delta\gamma$ and/or ipd. For example, viewer 122 (FIG. 1) may provide either or both of these values to graphical system 100 (FIG. 1). Alternatively, graphical system 100 (FIG. 1) may measure the $\delta\gamma$ and/or the ipd of viewer 122 (FIG. 1).

Graphical system 100 (FIG. 1) may also implement monoscopic depth cues in the rendered left-eye and right-eye images. These monoscopic depth cues may provide a priori depth information based at least in part on the experience of viewer 122 (FIG. 1). Note that the monoscopic depth cues may complement the effect of image parallax and motion parallax in triggering stereopsis. Notably, the monoscopic depth cues may include: relative sizes/positions (or geometric perspective), lighting, shading, occlusion, textural gradients, and/or depth cueing.

As noted previously, a geometric-perspective monoscopic depth cue (which is sometimes referred to as a 'rectilinear perspective' or a 'photographic perspective') may be based at least in part on the experience of viewer 122 (FIG. 1) that the size of the image of an object projected by the lens of the eye onto the retina is larger when the object is closer and is smaller when the object is further away. This reduced visibility of distant object (for example, by expanding outward from a focal point, which is related to the frustum) may define the relationship between foreground and background objects. If the geometric perspective is exaggerated, or if there are perspective cues such as lines receding to a vanishing point, the apparent depth of an image may be enhanced, which may make the image easier to view. While geometric perspective is not used in an exemplary embodiment of graphical system 100 (FIG. 1), in other embodiments geometric perspective may be used to complement the stereopsis scaling because it also enhances the stereopsis. For example, the frustum may be used to scale objects based at least in part on their distance z from viewer 122 (FIG. 1).

A lighting monoscopic depth cue may be based at least in part on the experience of viewer 122 (FIG. 1) that bright objects or objects with bright colors appear to be nearer than dim or darkly colored objects. In addition, the relative positions of proximate objects may be perceived by viewer 122 (FIG. 1) based at least in part on how light goes through the presented scene (e.g., solid objects versus non-solid objects). This monoscopic depth cue may be implemented by defining the position of a light source, defining transfer functions of the objects, and using the frustum. A similar monoscopic depth cue is depth cueing, in which the intensity of an object is proportional to the distance from viewer 122 in FIG. 1 (which may also be implemented using the frustum).

Shading may provide a related monoscopic depth cue because shadows cast by an object can make the object appear to be resting on a surface. Note that both lighting and shading may be dependent on a priori knowledge of viewer 122 (FIG. 1) because they involve viewer 122 (FIG. 1) understanding the light-source position (or the direction of the light) and how shadows in the scene will vary based at least in part on the light-source position.

Occlusion (or interposition) may provide a monoscopic depth cue based at least in part on the experience of viewer 122 (FIG. 1) that objects that are in front of others will occlude the objects that are behind them. Once again, this effect may be dependent on a priori knowledge of viewer 122 (FIG. 1). Note that lighting, shading and occlusion may also define and interact with motion parallax based at least in part on how objects are positioned relative to one another as viewer 122 (FIG. 1) moves relative to display 114 (FIG. 1). For example, the focal point of the light illuminating the object in a scene may change with motion and this change may be reflected in the lighting and the shading (similar to what occurs when an individual is moving in sunlight). Furthermore, the occlusion may be varied in a manner that is consistent with motion of viewer 122 (FIG. 1).

As described previously, the transfer functions that may be used to implement occlusion may be defined in graphical system 100 (FIG. 1) prior to graphics engine 112 in FIG. 1 (for example, by data engine 110 in FIG. 1). The transfer functions for objects may be used to modify the greyscale intensity of a given object after the projection on to the 2D viewing plane. Notably, during the projection on to the 2D viewing plane the average, maximum or minimum greyscale intensity projected into a given voxel may be used, and then may be modified by one or more transfer functions. For example, three sequential voxels in depth may have intensities of 50 to 100, −50 to 50, and −1000 to −50. These intensities may be modified according to a transfer function in which: greyscale values between 50 and 100 may have 0% intensity; greyscale values between −50 to 50 may have 100% intensity; and greyscale values between −1000 to −50 may have 50% intensity. In this way, the perspective may emphasize the second voxel and, to a lesser extent, the third voxel. In another example, transfer functions may be used to illustrate blood so that blood vessels appear filled up in the stereoscopic images, or to hide blood so that blood vessels appear open in the stereoscopic images.

Textural gradients for certain surfaces may also provide a monoscopic depth cue based at least in part on the experience of viewer 122 (FIG. 1) that the texture of a material in an object, like a grassy lawn or the tweed of a jacket, is more apparent when the object is closer. Therefore, variation in the perceived texture of a surface may allow viewer 122 (FIG. 1) to determine near versus far surfaces.

Computer System

Figure 6:
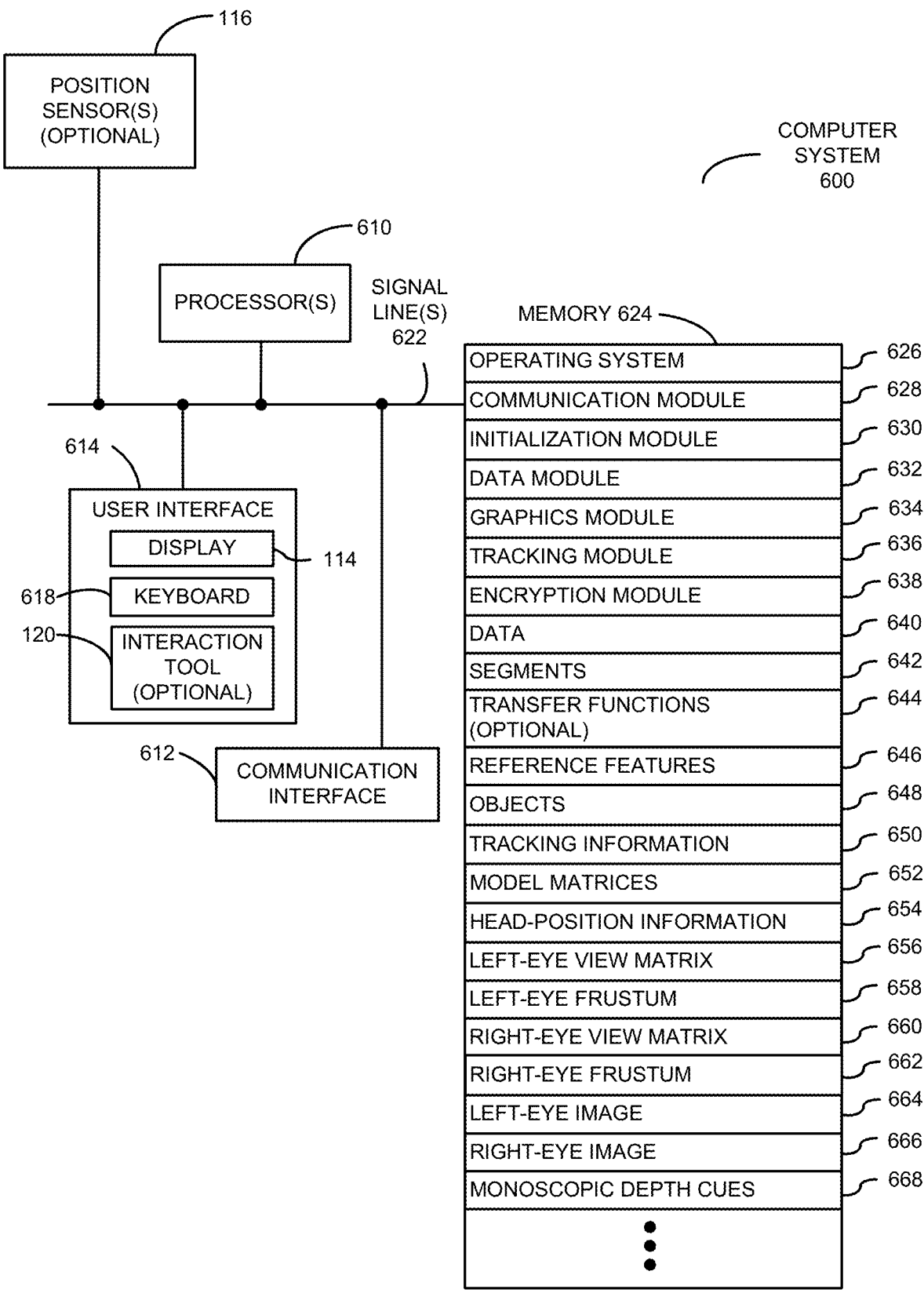
FIG. 6 is a block diagram illustrating a computer system in accordance with an embodiment of the present disclosure.

FIG. 6 presents a drawing of a computer system 600 that implements at least a portion of graphical system 100 (FIG. 1). This computer system includes one or more processing units or processors 610, a communication interface 612, a user interface 614, and one or more signal lines 622 coupling these components together. Note that the one or more processors 610 may support parallel processing and/or multi-threaded operation, the communication interface 612 may have a persistent communication connection, and the one or more signal lines 622 may constitute a communication bus. In some embodiments, the one or more processors 610 include a Graphics Processing Unit. Moreover, the user interface 614 may include: a display 114, a keyboard 618, and/or an optional interaction tool 120 (such as a stylus, a pointer a mouse and/or a sensor or module that detects displacement of one or more of the user's fingers and/or hands).

Memory 624 in computer system 600 may include volatile memory and/or non-volatile memory. More specifically, memory 624 may include: ROM, RAM, EPROM, EEPROM, flash memory, one or more smart cards, one or more magnetic disc storage devices, and/or one or more optical storage devices. Memory 624 may store an operating system 626 that includes procedures (or a set of instructions) for handling various basic system services for performing hardware-dependent tasks. Memory 624 may also store procedures (or a set of instructions) in a communication module 628. These communication procedures may be used for communicating with one or more computers and/or servers, including computers and/or servers that are remotely located with respect to computer system 600.

Memory 624 may also include program instructions (or sets of instructions), including: initialization module 630 (or a set of instructions), data module 632 (or a set of instructions) corresponding to data engine 110 (FIG. 1), graphics module 634 (or a set of instructions) corresponding to graphics engine 112 (FIG. 1), tracking module 636 (or a set of instructions) corresponding to tracking engine 118 (FIG. 1), and/or encryption module 638 (or a set of instructions). Note that one or more of the program instructions (or sets of instructions) may constitute a computer-program mechanism. The program instructions may be used to perform or implement: initialization, object identification and segmentation, virtual instruments, prehension and motion parallax, as well as the image processing rendering operations described previously.

Initialization

During operation, initialization module 630 may define parameters for image parallax and motion parallax. Notably, initialization module 630 may initialize a position of a camera or an image sensor in display 114 in a monoscopic view matrix by setting a position equal to the offset d between the viewing plane and the near plane of the frustum. (Alternatively, there may be a camera or an image sensor in optional interaction tool 120 that can be used to define the perspective. This may be useful in surgical planning.) For example, the offset d may be 1 ft or 0.3 m. Moreover, the focal point (0, 0, 0) may be defined as the center of the (x, y, z) plane and the +y axis may be defined as the 'up' direction.

Furthermore, the near and far planes in the frustum may be defined relative to the camera (for example, the near plane may be at 0.1 m and the far plane may be between 1.5-10 m), the right and left planes may be specified by the width in size 126 (FIG. 1) of display 114, and the top and bottom planes may be specified by the height in size 126 (FIG. 1) of display 114. Initialization module 630 may also define the interpupillary distance ipd equal to a value between 62 and 65 mm (in general, the ipd may vary between 55 and 72 mm). Additionally, initialization module 630 may define the display rotation angle θ (for example, θ may be 30°, where horizontal in 0°) and may initialize a system timer (sT) as well as tracking module 636 (which monitors the head position of viewer 122 in FIG. 1, the position of optional interaction tool 120, the position of one or more digits, a hand or an arm of viewer 122 in FIG. 1, and which may monitor the gaze direction of viewer 122).

Then, initialization module 630 may perform prehension initialization. Notably, start and end points of optional interaction tool 120 and/or the one or more digits, the hand or the arm of viewer 122 in FIG. 1 may be defined. The start point may be at (0, 0, 0) and the end point may be at (0, 0, tool length), where tool length may be 15 cm.

Next, the current (prehension) position of optional interaction tool 120 and/or the one or more digits, the hand or the arm of viewer 122 in FIG. 1 (PresPh) may be defined, with a corresponding model matrix defined as an identity matrix. Moreover, a past (prehension) position of optional interaction tool 120 and/or the one or more digits, the hand or the arm of viewer 122 in FIG. 1 (PastPh) may be defined with a corresponding model matrix defined as an identity matrix. Note that prehension history of position and orientation of optional interaction tool 120 and/or the one or more digits, the hand or the arm of viewer 122 in FIG. 1 can be used to provide a video of optional interaction tool 120 and/or the one or more digits, the hand or the arm movements, which may be useful in surgical planning.

In addition, initialization module 630 may initialize monoscopic depth cues. In some embodiments, a plane 25-30% larger than the area of display 114 is used to avoid edge effects and to facilitate the stereopsis scaling described previously. In some embodiments, the stereopsis scaling is adapted for a particular viewer based at least in part on factors such as: age, the wavelength of light in display 114, sex, the display intensity, etc. Moreover, the monoscopic depth-cue perspective may be set to the horizontal plane (0, 0, 0), and the monoscopic depth-cue lighting may be defined at the same position and direction as the camera in the view matrix.

Object Identification and Segmentation

Figure 7:
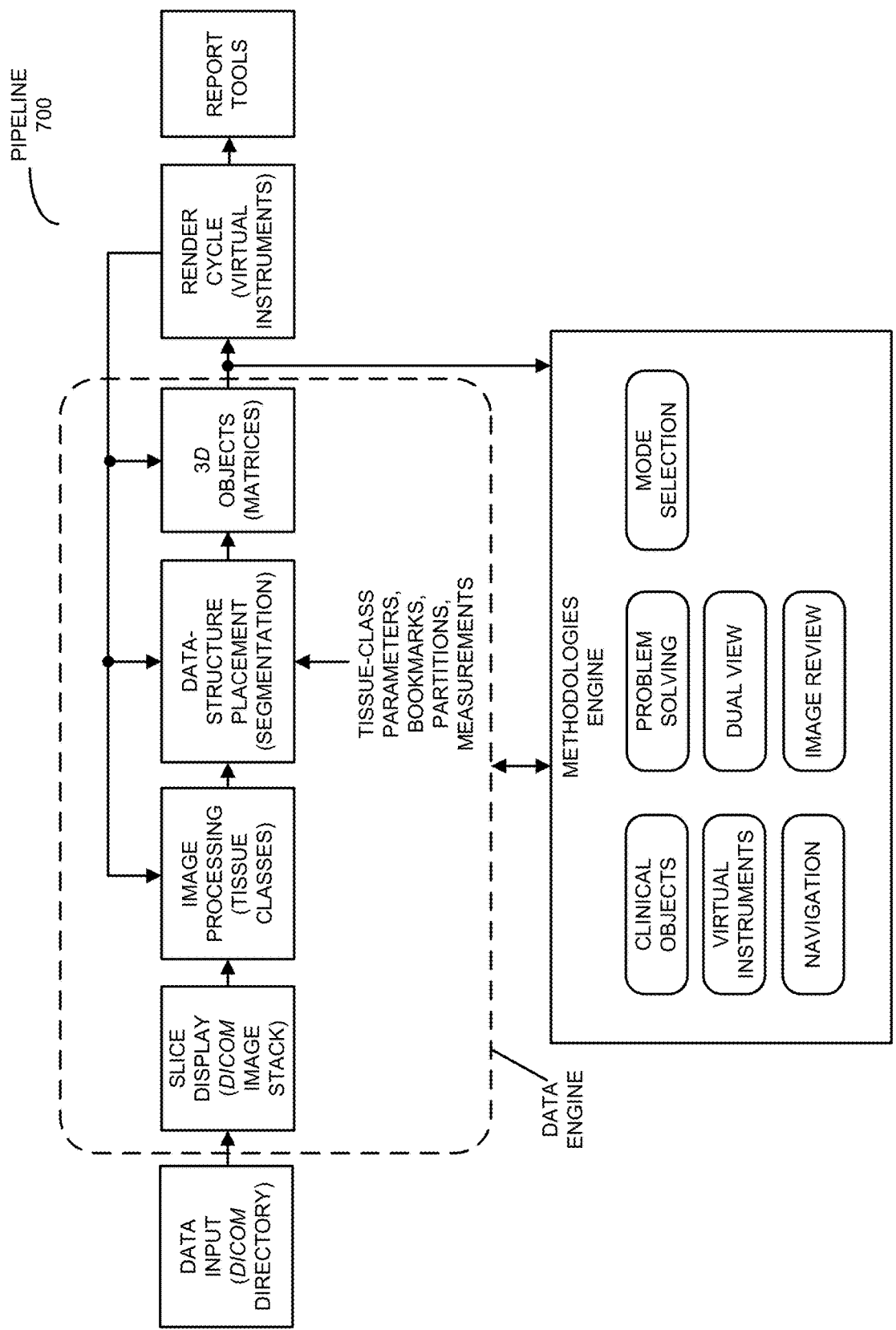
FIG. 7 is a block diagram illustrating a pipeline performed by the computer system of FIG. 6 in accordance with an embodiment of the present disclosure.

After the initialization is complete, data module 632 and graphics module 634 may define or may receive information from the user specifying: segments 642, optional transfer functions 644, reference features 646 and objects 648 in data 640. These operations are illustrated in FIG. 7, which presents a drawing illustrating a pipeline 700 performed by computer system 600 in FIG. 6. Notably, data 640 in FIG. 6 may include a DICOM directory with multiple DICOM images (i.e., source image data from one or more imaging devices), such as a series of 2D images that together depict a volumetric space that contains the anatomy of interest. Data module 632 in FIG. 6 may parse DICOM labels or tags associated with the DICOM images so that a number of images in the series are extracted along with their associated origin coordinate, orientation and voxel x, y and z spacing. (Note that, in general, data 640 may be isometric or non-isometric, i.e., dx, dy and dz may be the same or may be different from each other.) Then, each image of the series is loaded according to its series number and compiled as a single 3D collection of voxels, which includes one of more 3D objects 648 in FIG. 6 (and is sometimes referred to as a 'DICOM image object' or a 'clinical object').

Next, data module 632 may dimensionally scale (as opposed to the stereopsis scaling) the DICOM image object. For example, data module 632 may scale all the x voxels by multiplying their spacing value by 0.001 to assure the dimensions are in millimeters. Similarly, data module 632 may scale all the y voxels and all the z voxels, respectively, by multiplying their spacing values by 0.001 to assure the dimensions are in millimeters. This dimensional scaling may ensure that the voxels have the correct dimensions for tracking and display.

Furthermore, data module 632 may map the DICOM image object on to a plane with its scaled dimensions (i.e., the number of x voxels and the number of y voxels) and may be assigned a model matrix with its original orientation and origin. In some embodiments, graphics engine 634 in FIG. 6 optionally displays a stack of images (which is sometimes referred to as a 'DICOM image stack') corresponding to the DICOM image object in the plane.

Subsequently, via iterative interaction with graphics engine 634 and/or the user, data module 632 may aggregate or define several object lists that are stored in reference features 646 in FIG. 6. These object lists may include arrays of objects 648 that specify a scene, virtual instruments (or 'virtual instrument objects), or clinical objects (such as the DICOM image object), and may be used by graphics engine 634 to generate and render stereoscopic images (as described previously). A 'scene' includes 3D objects that delimit the visible open 3D space. For example, a scene may include a horizontal plane that defines the surface work plane on which all 3D objects in the DICOM image object are placed. Moreover, 'virtual instruments' may be a collection of 3D objects that define a specific way of interacting with any clinical target, clinical anatomy or clinical field. Notably, a virtual instrument includes: a 'representation' that is the basic 3D object elements (e.g., points, lines, planes) including a control variable; and an 'instrument' that implements the interaction operations based at least in part on its control variables to its assigned clinical target, clinical anatomy or clinical field. Note that a 'clinical field' may be a clinical object that defines a region within the DICOM image object that contains the anatomy of interest; 'clinical anatomy' may be a clinical object that defines the organ or tissue that is to be evaluated; and a 'clinical target' may be a clinical object that defines the region of interest of anatomy that is the candidate to be diagnosed or evaluated. (Clinical fields, clinical anatomy and clinical targets may be determined by the user and/or data module 632 during a segmentation process, which is described further below.) Note that, in some embodiments, a virtual instrument includes a software-extension of optional interaction tool 120 and/or an appendage of viewer 122 in FIG. 1 (such as one or more digits, a hand or an arm), which can perform specific interaction tasks or operations. Furthermore, note that the user: cannot interact with scenes; may only be able to interact with virtual instruments through their control variables; and may have free interaction with clinical objects.

During iterative interaction, data module 632 may perform image processing on the DICOM image object to identify different levels of organ or tissue of interest. Notably, for the clinical field, the DICOM image object may be processed to identify different tissue classes (such as organ segments, vessels, etc.) as binary 3D collections of voxels based at least in part on the voxel values, as well as the boundaries between them. In the discussion that follows, a probability-mapping technique is used to identify the tissue classes. However, in other embodiments, different techniques may be used, such as: a watershed technique, a region-growing-from-seeds technique, or a level-set technique.

In the probability-mapping technique, a probability map (P) is generated using a 3D image with the same size as one of the DICOM images. The values of P may be the (estimated) probability of voxels being inside, outside and at the edge of the organ of interest. For each voxel, P may be obtained by computing three (or more) probabilities of belonging to tissue classes of interest, such as: voxels inside the organ (tissue class w1), voxels outside the organ (tissue class w2), and voxels at the interface between organs (tissue class w3). For a given voxel, P may be determined from the maximum of these three probabilities. Note that each probability may be calculated using a cumulative distribution function, e.g., $$F(x, x_o, \gamma) = \frac{1}{\pi} \cdot \arctan\left(\frac{x - x_o}{\gamma}\right) + \frac{1}{2},$$

where $x_o$ is the density of the tissue class, x is the density of the tested voxel, and $\gamma$ is a scale parameter of the distribution or the half-width at half-maximum.

The voxels at the interface between the tissue classes may be calculated for a neighborhood of voxels as being part of tissue class w1 or tissue class w2, and then averaging the result. Pseudo-code for this calculation for an omni-directional configuration with 27 neighboring voxels is shown in Table 1.

TABLE 1

```
for each voxel (x, y, z) do
    sum=0;
    for i = -1 to 1 do
        for j = -1 to 1 do
            for k = -1 to 1 do
                sum += P(w1j(x + i, y + j, z + k));
                sum += P(w2j(x + i, y + j, z + k));
```

TABLE 1-continued

```
            end;
        end;
    end;
    P(w3j(x, y, z)) = sum/27;
end
```

Additionally, during the iterative interaction data module 632 may perform image processing on the DICOM image object to identify the clinical anatomy. Notably, using the organ binary mask a ray-casting technique can be applied to generate a volume image of the organ of interest, such as the liver or another solid organ. Furthermore, using the boundary-voxel mask, a surface can be generated of the tissue using a marching-cube technique, such as the surface of a vessel (e.g., the large intestine or an artery). Note that other surfaces or ray-casting volumes can be generated from the segmented data.

In an exemplary embodiment, the determined clinical field may be the chest, the clinical anatomy may be the aorta, and the clinical target may be the aortic valve. Alternatively, the clinical field may be the abdomen, the clinical anatomy may be the colon, and the clinical target may be the one or more polyps.

After the image processing, data module 632 may perform the segmentation process (including data-structure processing and linking) to identify landmarks and region-of-interest parameters. The objective of the segmentation process is to identify functional regions of the clinical anatomy to be evaluated. This may be accomplished by an articulated model, which includes piecewise rigid parts for the anatomical segments coupled by joints, to represent the clinical anatomy. The resulting segments 642 in FIG. 6 may each include: a proximal point (S) location specified by the DICOM image-voxel index coordinate ($i_1$, $j_1$, $k_1$); a distal point (D) location specified by the DICOM image-voxel index coordinate ($i_2$, $j_2$, $k_2$); a central point (C) location specified by the DICOM image-voxel index coordinate ($i_3$, $j_3$, $k_3$), which may be the half point of the Euclidean distance between S and D; image-voxel index bounds (B) of the region of interest surrounding the central point including the proximal and distal points ($i_{min}$, $i_{max}$, $j_{min}$, $j_{max}$, $k_{min}$, $k_{max}$); and the corresponding world x, y, z coordinates of the central point and the region bounds locations calculated by accounting for the x, y, z voxel spacing of the source DICOM image. In general, segments 642 may be determined using an interactive segmentation technique with the user and/or a computer-implemented segmentation technique.

In the interactive segmentation technique, the user may select or specify n voxel index locations from the clinical field, which may be used to define the central points (Cs). Then, a 3D Voronoi map (and, more generally, a Euclidean-distance map) may determine regions around each of the selected index locations.

For each of the Voronoi regions and each of the n voxel indexes, data module 632 may obtain: the minimum voxel index along the x axis of the DICOM image ($i_{min}$); the maximum voxel index along the x axis of the DICOM image ($i_{max}$); the minimum voxel index along the y axis of the DICOM image ($j_{min}$); the maximum voxel index along they axis of the DICOM image ($j_{max}$); the minimum voxel index along the z axis of the DICOM image ($k_{min}$); and the maximum voxel index along the z axis of the DICOM image ($k_{max}$). Next, data module 632 may define: the proximal S point as $i_{min}$, $j_{min}$, $k_{min}$; and the distal D point as $i_{max}$, $j_{max}$, $k_{max}$. Moreover, data module 632 may generate a list of 3D objects (such as anatomical segments) of the clinical anatomy based at least in part on these values and may add these 3D objects to the object list of clinical objects in reference features 646 for use by graphics module 634.

Using the interactive or the computer-based segmentation technique, the surface of the colon may be a single object or may be sub-divided into six segments or more. Depending on the tortuosity of the colon, this calculation may involve up to 13 iterations in order to obtain segments with the desired aspect ratios.

Moreover, the articulated model may facilitate: fast extraction of regions of interest, reduced storage requirements (because anatomical features may be described using a subset of the DICOM images or annotations within the DICOM images), faster generating and rendering of True 3D stereoscopic images with motion parallax and/or prehension, and a lower cost for the graphical system.

Virtual Instruments

As described previously in the discussion of image processing and rendering operations, graphics module 634 may generate 3D stereoscopic images. Furthermore, prior to rendering these 3D stereoscopic images and providing them to display 114, stereopsis scaling may be performed to enhance or optimize the stereo acuity of the user based at least in part on the maximum and minimum scale factors (i.e., the range of scaling) that can be applied to the anatomical segments $dz_{min}$ and $dz_{max}$. During the rendering, once the anatomy has been adequately segmented and linked, graphics module 634 may also implement interaction using one or more virtual instruments. For example, a virtual instrument may allow the user to navigate the body parts, and to focus on and to evaluate a segment of an individual's anatomy, allowing the user to optimize workflow. In the discussion that follows, a given virtual instrument may include any of the features or operations described below. Thus, a given virtual instrument may include one or more of these features or operations, including a feature or operation that is included in the discussion of another virtual instrument.

Each virtual instrument includes: a 'representation' which is the basic object elements (points, lines, planes, other 3D objects, etc.) including a control variable; and an 'instrument' which implements the interaction operations based at least in part on its control variables to its assigned clinical target, clinical anatomy or clinical field. While a wide variety of virtual instruments can be defined (such as a pointer or a wedge), in the discussion that follows a dissection cut plane, a bookmark to a region of interest, a problem-solving tool that combines a 3D view with a 2D cross-section, and an 'intuitive 2D' approach that allows the viewer to scroll through an array of 2D images using stylus are used as illustrative examples.

For the cut-plane virtual instrument, the representation includes: an origin point (Origin) that defines an origin $x_o$, $y_o$, $z_o$ position of the cut plane; point 1 that, in conjunction with the origin point, defines axis 1 ($a_1$) of the cut plane; and point 2 that, in conjunction with the origin point, defines axis 2 ($a_2$) of the cut plane. The normal to the cut plane points in the direction of the cross product of $a_1$ and $a_2$. Moreover, the center point (Center Point) is the control point of the cut plane.

Notably, $$Center[x]=Origin[x_o]+0.5(a_1[x]+a_2[x]),$$

$$Center[y]=Origin[y_o]+0.5(a_1[y]+a_2[y]),$$

and $$Center[z]=Origin[z_o]+0.5(a_1[z]+a_2[z]).$$

The user can control the cut plane by interacting with the center point, and can translate and rotate the cut plane using optional interaction tool 120 and/or motion of one or more digits, a hand or an arm in FIG. 6. For example, the user can control a cut plane to uncover underlying anatomical features, thereby allowing the rest of the anatomical segment to be brought into view by rotating the anatomical segment. Note that the cut plane may modify the bounding-box coordinates of the anatomical segment by identifying the intersection points of the cut plane to the bounding box in the direction of the normal of the cut plane.

For the bookmark virtual instrument, the representation includes: point 1 that defines $x_{min}$, $y_{min}$ and $z_{min}$; point 2 that defines $x_{max}$, $y_{max}$ and $Z_{max}$. The bookmark may be specified by the center point and the bounds of the box ($x_{min}$, $x_{max}$, $y_{min}$, $y_{max}$, $z_{min}$, $z_{max}$). Moreover, the center point (Center Point) is the control point of the region of interest. Notably, $$Center[x]=0.5(x_{max}-x_{min}),$$

$$Center[y]=0.5(y_{max}-y_{min}),$$

and $$Center[z]=0.5(z_{max}-Z_{min}).$$

The user can control the bookmark by placing it at a center point of any clinical object with a box size equal to 1, or by placing a second point to define a volumetric region of interest. When the volumetric region of interest is placed, that region can be copied for further analysis. Note that using a bookmark, the user can specify a clinical target that can be added to the object list of clinical objects for use by graphics module 634.

For the problem-solving virtual instrument, the representation combines a bookmark to a 3D region of interest and a cut plane for the associated 2D projection or cross-section. This representation is summarized in Table 2.

TABLE 2

| 2D Cross-Section | 3D Region of Interest |
| --- | --- |
| The origin point defines the position of a cut plane ($x_o$, $y_o$, $z_o$). Point 1 defines axis 1 ($a_1$) of the cut plane. Point 2 defines axis 2 ($a_2$) of the cut plane. The normal to the cut plane points in the direction of the cross product of $a_1$ with $a_2$. The center point is the control point of the cut plane. | Point 1 defines $x_{min}$, $y_{min}$ and $z_{min}$. Point 2 defines $x_{max}$, $y_{max}$ and $z_{max}$. The bookmark is defined by the center point and the bounds of the box ($x_{min}$, $x_{max}$, $y_{min}$, $y_{max}$, $z_{min}$, $z_{max}$). The center point is the control point. |

The user can control the problem-solving virtual instrument to recall a bookmarked clinical target or a selected region of interest of a 3D object and can interact with its center point. In this case, the surface of the 3D object may be transparent (as specified by one of optional transfer functions 644 in FIG. 6). The 2D cross-section is specified by a cut plane (defined by the origin, point 1 and point 2) that maps the corresponding 2D DICOM image of the cut plane within the region of interest. By interacting with the 2D cross-section center point, the user can determine the optimal 2D cross-sectional image of a particular clinical target. Note that the problem-solving virtual instrument allows the user to dynamically interact with the 3D stereoscopic image and at least one 2D projection. As the user interacts with objects in these images, the displayed images may be dynamically updated. Furthermore, instead of merely rotating an object, the user may be able to 'look around' (i.e., motion parallax in which the object rotates in the opposite direction to the rotation of the user relative to the object), so that they can observe behind an object, and concurrently can observe the correct 2D projection.

Figure 8A:
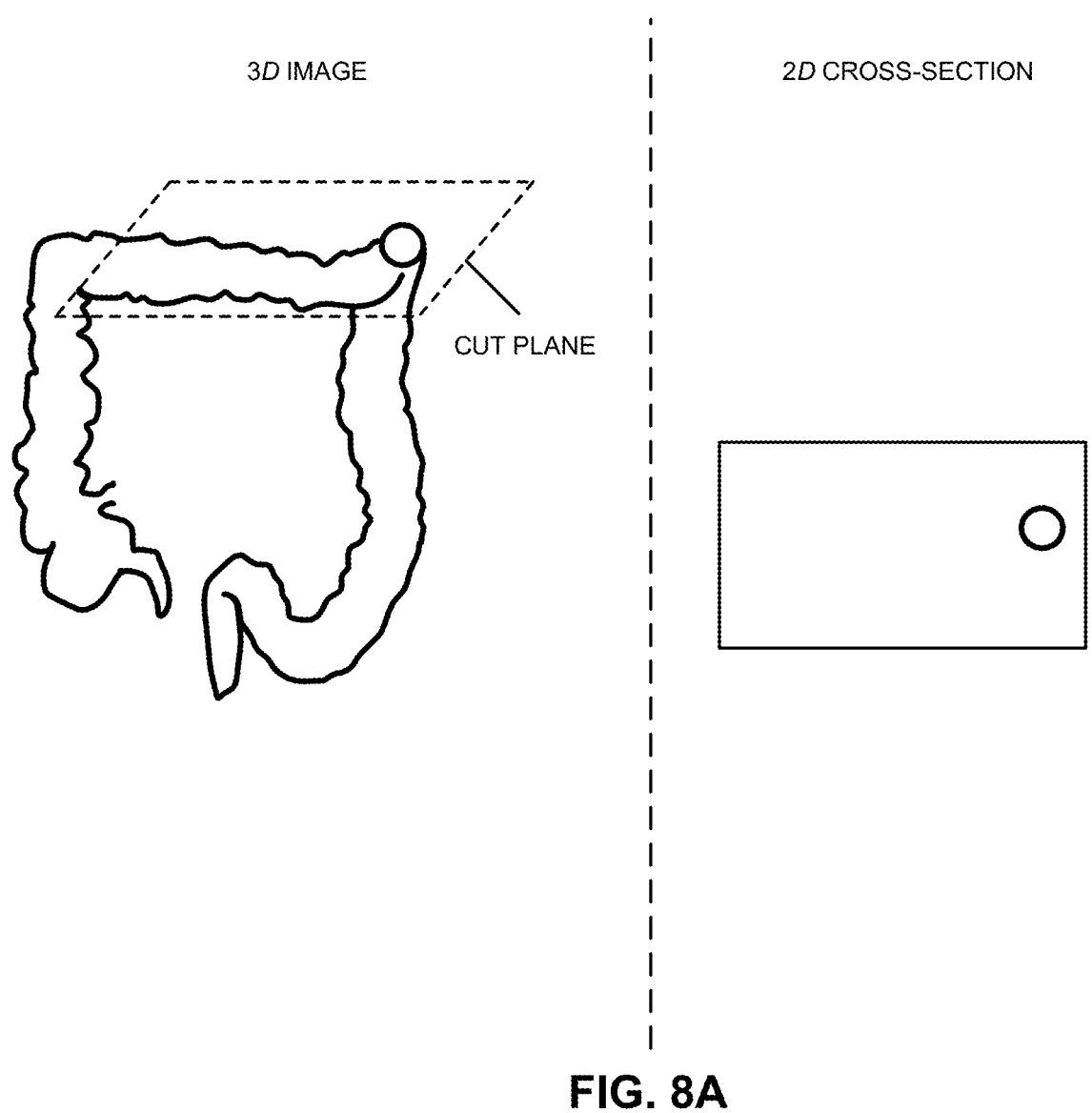
FIG. 8A is a drawing illustrating a display in the graphical system of FIG. 1 in accordance with an embodiment of the present disclosure.
Figure 8B:
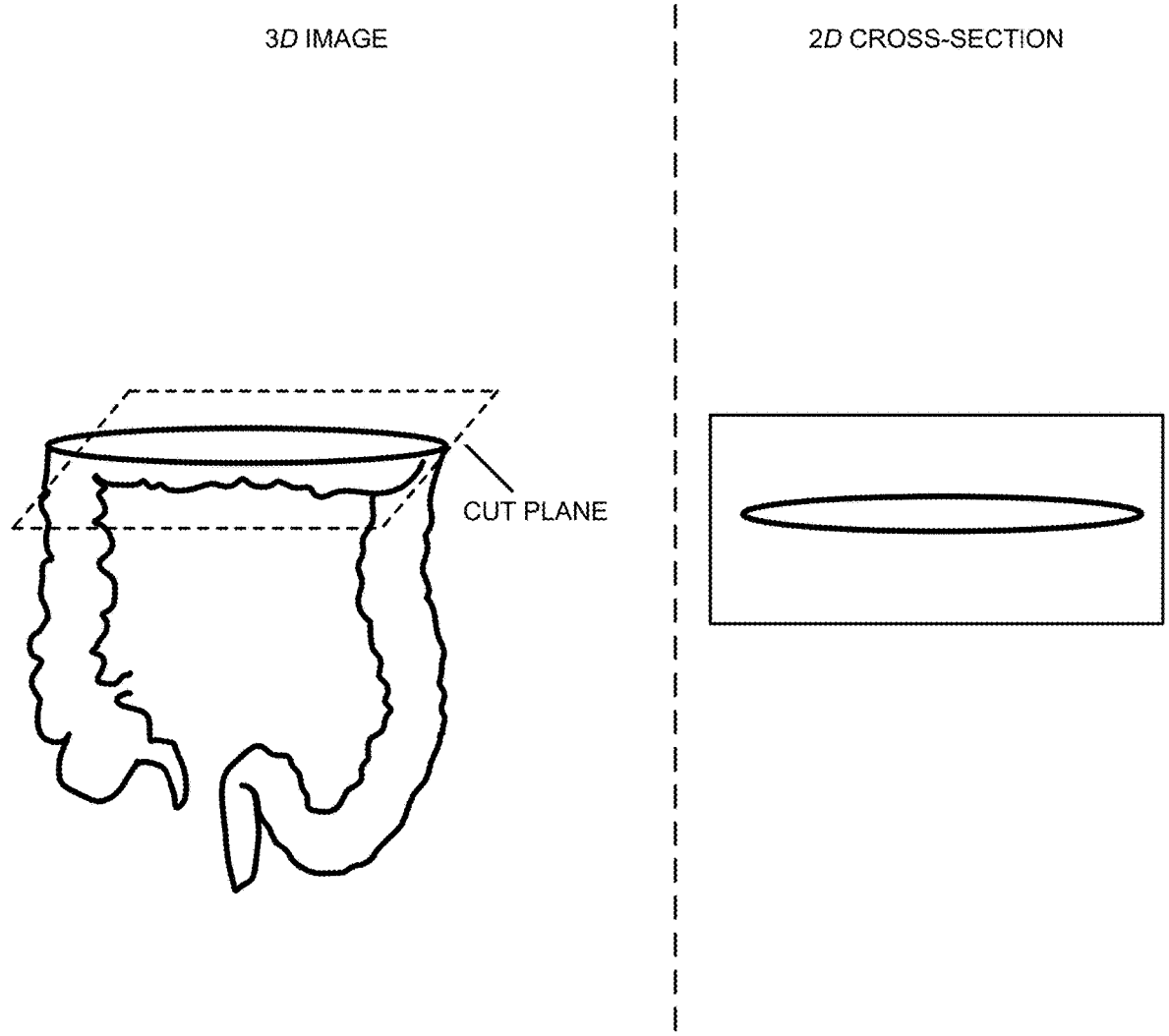
FIG. 8B is a drawing illustrating a display in the graphical system of FIG. 1 in accordance with an embodiment of the present disclosure.
Figure 8C:
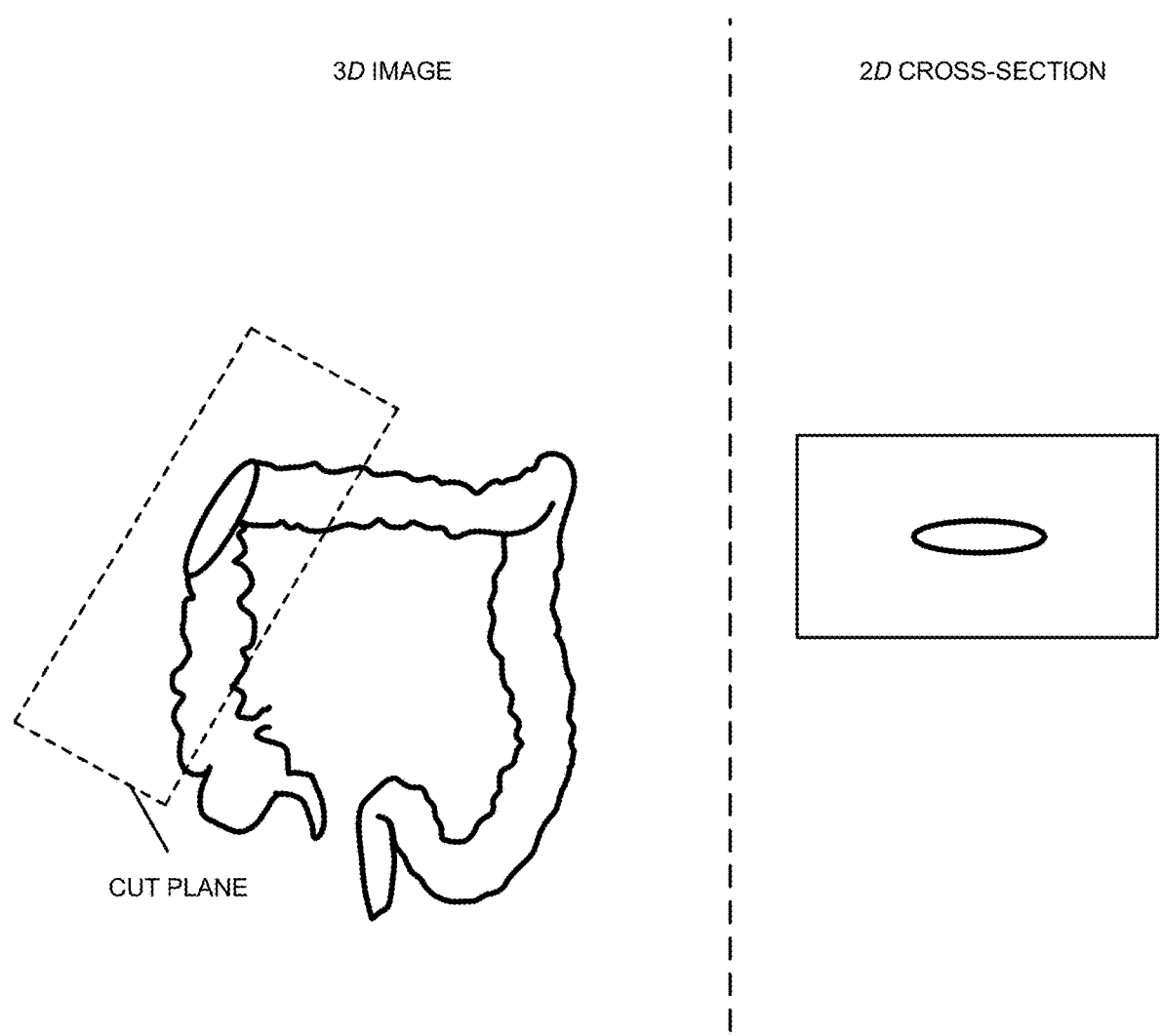
FIG. 8C is a drawing illustrating a display in the graphical system of FIG. 1 in accordance with an embodiment of the present disclosure.

This operation of the problem-solving virtual instrument is illustrated in FIGS. 8A-C, which shows the display of a 3D stereoscopic image and 2D projections side by side (such as on display 114 in FIGS. 1 and 6). When the user moves, changes their viewing direction or perspective and/or interacts with the object (in this case a rectangular cube) in the 3D stereoscopic image, graphics module 634 in FIG. 6 dynamically updates the 2D projection. This may allow the user to look around the object (as opposed to rotating it along a fixed axis). Moreover, by providing accurate and related 2D and 3D images, the problem-solving virtual instrument may allow a physician to leverage their existing training and approach for interpreting 2D images when simultaneously viewing 3D images.

Note that the ability to define an arbitrary cut plane through a 3D stereoscopic image and/or to present an associated 2D projection can facilitate manual and/or automated annotation. For example, computer system 600 may provide, on a display, a 3D image of a portion of an individual, where the 3D image has an initial position and orientation. Then, computer system 600 may receive information specifying a 2D plane in the 3D image, where the 2D plane has an arbitrary angular position relative to the initial orientation (such as an oblique angle relative to a symmetry axis of the individual). In response, computer system 600 may translate and rotate the 3D image so that the 2D plane is presented in a reference 2D plane of the display with an orientation parallel to an orientation of the reference 2D plane, where, prior to the translating and the rotating, the angular position is different than that of the reference 2D plane and is different from a predefined orientation of slices in the 3D image. Note that the 2D plane may be positioned at a zero-parallax position so that 3D information in the 2D plane is perceived as 2D information. Moreover, note that a normal of the reference 2D plane may be perpendicular to a plane of the display. Next, computer system 600 may receive information specifying the detailed annotation in the 2D plane, where the detailed annotation includes at least one of: a size of the anatomical structure based at least in part on annotation markers, an orientation of the anatomical structure, a direction of the anatomical structure and/or a location of the anatomical structure. Moreover, after the annotation is complete, computer system 600 may translate and rotate the 3D image back to the initial position and orientation.

Similarly, in some embodiments one or more of the aforementioned annotation operations may be repeated to provide multi-point annotation. For example, computer system 600 may iteratively performs a set of operations for a group of marker points. Notably, for a given marker point, computer system 600 may provide, on a display, a given 3D image (such as a first 3D image) of a portion of an individual, where the given 3D image has an initial position and an initial orientation. Then, computer system 600 may receive information specifying a given 2D plane in the given 3D image, where the given 2D plane has an angular position relative to the initial orientation. Moreover, computer system 600 may translate and rotate the given 3D image so that the given 2D plane is presented on a reference 2D plane of the display with an orientation parallel to the reference 2D plane (so that the normal to the given 2D plane is parallel to the normal of the reference 2D plane), where, prior to the translating and the rotating, the angular position of the given 2D plane is different from an angular position of the reference 2D plane and is different from a predefined orientation of slices in the given 3D image. Next, computer system 600 may receive annotation information specifying detailed annotation in the given 2D plane of the given marker point. After the annotation of the given marker point is complete, computer system 600 may translate and rotate the given 3D image back to the initial position and the initial orientation.

In some embodiments, instead of translate and rotate the given 3D image back to the initial position and the initial orientation after the annotation of each of the given marker points, computer system 600 continues with operations associated with one or more subsequent marker points. For example, after the annotation of a first marker point is complete, computer system 600 may provide, on the display, a second 3D image of a portion of an individual, where the second 3D image is generated by translating image data along a normal direction to the first 2D plane by a predefined distance. Then, computer system 600 may receive annotation information specifying detailed annotation in a second 2D plane of a second marker point. These operations may be repeated for zero or more additional marker points. Moreover, after the annotation of the last marker point is complete, computer system 600 may translate and rotate the last 3D image back to the initial position and the initial orientation.

Note that the given 3D image may be different for at least some of the marker points in the group of marker points. Moreover, at least a pair of the marker points in the group of marker points may describe one of: a linear distance, or a 3D vector. Furthermore, at least three of the marker points in the group of marker points may describe one of: a plane, or an angle between two intersecting lines. Additionally, at least some of the marker points in the group of marker points may describe one of: a poly-line, an open contour, a closed contour, or a closed surface.

While the preceding embodiments illustrated the display of a 3D image and/or a 2D image associated with a 2D plane (such as a cut plane), in other embodiments the 3D image and/or the 2D image may be simulated. For example, computer system 600 may generate a simulated 2D fluoroscopy image based at least in part on data in a predetermined 3D image associated with an individual's body, and relative positions of a fluoroscopy source in a C-arm measurement system, a detector in the C-arm measurement system and a predefined cut plane in the individual's body. Then, computer system 600 may provide or display the simulated 2D fluoroscopy image with a 3D context associated with the predefined cut plane in the individual's body, where the 3D context may include a stereoscopic image with image parallax of at least a portion of the individual's body based at least in part on the 3D model of the individual's body.

Note that generating the simulated 2D fluoroscopy image may involve a forward projection. Moreover, generating the simulated 2D fluoroscopy image may involve calculating accumulated absorption corresponding to density along lines, corresponding to X-ray trajectories, through pixels in the predetermined 3D image.

Furthermore, the 3D context may include: a slice, based at least in part on a 3D model of the individual's body, having a thickness through the individual's body that includes the predefined cut plane. Additionally, the 3D context may include at least partial views of anatomical structures located behind the predefined cut plane via at least partial transparency of stereoscopic image.

In some embodiments, computer system 600 may provide, based at least in part on the 3D model, a second stereoscopic image with image parallax adjacent to the simulated 2D fluoroscopy image with the 3D context. The second stereoscopic image may include graphical representations of the relative positions of the fluoroscopy source in the C-arm measurement system, the detector in the C-arm measurement system and the predefined cut plane.

Note that the 3D context and the simulated 2D fluoroscopy image may be superimposed.

Moreover, computer system 600 may receive a user-interface command associated with user-interface activity. In response, computer system 600 may provide the simulated 2D fluoroscopy image without the 3D context.

Furthermore, an orientation and a location of the predefined cut plane may be specified based at least in part on: a position of the fluoroscopy source and the detector in the C-arm measurement system; and/or a received user-interface command associated with user-interface activity.

The intuitive 2D virtual instrument presents a 2D image that is displayed as the viewer scrolls through an array of 2D images using a stylus (and, more generally, the optional interaction tool) or a scroll bar. This virtual instrument can improve intuitive understanding of the 2D images.

The intuitive 2D virtual instrument uses a 3D volumetric image or dataset that includes the 2D images. These 2D images include a collection of voxels that describe a volume, where each voxel has an associated 4×4 model matrix. Moreover, the representation for the intuitive 2D virtual instrument is a fixed cut plane, which specifies the presented 2D image (i.e., voxels in the dataset that are within the plane of interaction with the cut plane). The presented 2D image is at position (for example, an axial position) with a predefined center (x, y, z position) and bounds ($x_{min}$, $x_{max}$, $y_{min}$, $y_{max}$, $z_{min}$, $z_{max}$). The cut plane, which has a 4×4 rotation matrix with a scale of one, is a two-dimensional surface that is perpendicular to its rotation matrix. Note that the cut plane can be defined by: the origin of the cut plane (which is at the center of the presented 2D image), the normal to the current plane (which is the normal orientation of the presented 2D image), and/or the normal matrix N of the reference model matrix M for the presented 2D image (which defines the dimensions, scale and origin for all of the voxels in the presented 2D image), where N is defined as the transpose (inverse(M)). Another way to define the cut plane is by using the forward (pF) and backward point (pB) of the stylus or the optional interaction tool. By normalizing the interaction-tool vector, which is defined as $$\frac{pF - pB}{|pF - pB|},$$

normal of the cut plane is specified, and the forward point of the stylus of the optional interaction tool specifies the center of the cut plane.

In the intuitive 2D virtual instrument, the normal of the cut plane defines the view direction in which anything behind the cut plane can be seen by suitable manipulation or interaction with the cut plane, while anything in front of the cut plane cannot be seen. Because the dataset for the intuitive 2D virtual instrument only includes image data (e.g., texture values) only the voxel values on the cut plane are displayed. Therefore, transfer functions and segmentation are not used with the intuitive 2D virtual instrument.

By translating/rotating the cut plane using the stylus (or the scroll bar), the viewer can display different oblique 2D image planes (i.e., different 2D slices or cross-sections in the dataset). If the viewer twists their wrist, the intuitive 2D virtual instrument modifies the presented 2D image (in a perpendicular plane to the stylus direction). In addition, using the stylus the viewer can go through axial, sagittal or coronal views in sequence. The viewer can point to a pixel on the cut plane and can push it forward to the front.

During interaction with the viewer, for the cut plane the intuitive 2D virtual instrument uses the stylus coordinates to perform the operations of: calculating a translation matrix (Tr) between the past and present position; calculating the rotation (Rm) between the past and present position; calculating the transformation matrix (Tm) equal to $-Tr \cdot Rm \cdot Tr$; and applying the transformation to the reference model matrix. Thus, the cut plane is only rotated, while translations forward or backward in the slides are canceled out. Similarly, for the presented 2D image, the intuitive 2D virtual instrument uses the stylus coordinates to perform the operations of: calculating a translation matrix (Tr) between the past and present position; calculating the rotation (Rm) between the past and present position; calculating the transformation matrix (Tm) equal to $Rm \cdot (-Tr)$; and applying the transformation to the reference model matrix. Thus, the presented 2D image includes translations (moving forward or backward in the slides) and includes a 2D slice at an arbitrary angle with respect to fixed (or predefined) 2D data slices based at least in part on manipulations in the plane of the cut plane.

Figure 9:
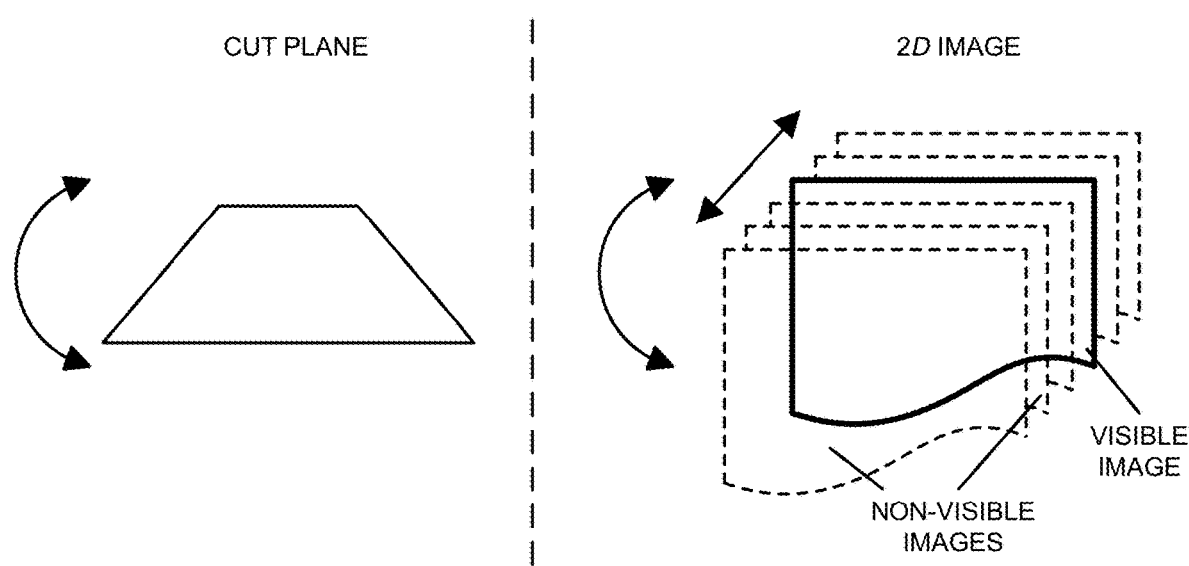
FIG. 9 is a drawing illustrating a virtual instrument in accordance with an embodiment of the present disclosure.

The interaction is illustrated in FIG. 9, which shows the cut plane and the presented 2D image side by side (such as on display 114 in FIGS. 1 and 6) for the intuitive 2D virtual instrument. (In addition, non-visible 2D images surrounding the presented 2D image are illustrated in FIG. 9 using dashed lines.) Based at least in part on manipulation of the stylus by the viewer (which can include rotations and/or translations), the cut plane is rotated, while the presented 2D image is translated and/or rotated to uncover voxels. Alternatively or additionally, different cut planes may be specified by bookmarks defined by the viewer (such as anatomical locations of suspected or potential polyps), and associated 2D images may be presented to the viewer when the viewer subsequently scrolls through the bookmarks.

While the preceding examples illustrated at least a 3D image and an associated 2D image being presented side by side, in other embodiments a user can use a virtual instrument to view either the 3D image or the 2D image in isolation.

Prehension and Motion Parallax

Referring back to FIG. 6, tracking module 636 may track the position of optional interaction tool 120 and/or one or more digits, a hand or an arm of viewer 122 (FIG. 1), for example, using the one or more optional position sensors 116. In the discussion that follows, the position of optional interaction tool 120 is used as an illustrative example. The resulting tracking information 650 may be used to update the position of optional interaction tool 120 (e.g., PastPh equals PresPh, and PresPh equals the current position of optional interaction tool 120). Graphics module 634 may use the revised position of the optional interaction tool 120 to generate a revised transformation model matrix for optional interaction tool 120 in model matrices 652.

Next, tracking module 636 may test if optional interaction tool 120 and/or the one or more digits, the hand or the arm of viewer 122 (FIG. 1) is touching or interfacing with one of objects 648 shown in display 114 (note, however, that in some embodiments viewer 122 in FIG. 1 cannot interact with some of reference features 646 using optional interaction tool 120). If yes, the position and orientation of optional interaction tool 120 may be modified, with a commensurate impact on the transformation model matrix in model matrices 652 for optional interaction tool 120. Notably, the translation to be applied to the one of objects 648 (Delta Vector) may be determined based at least in part on the x, y and z position of the tool tip (ToolTip) (which is specified by PresPh) and the x, y and z position where optional interaction tool 120 touches the one of objects 648 (ContactPoint) using DeltaVector[x]=ToolTip[x]−ContactPoint[x], DeltaVector[y]=ToolTip[y]−ContactPoint[y], and DeltaVector[z]=ToolTip[z]−ContactPoint[z].

The rotation to be applied may be determined using a local variable (in the form of a 4×4 matrix) called ROT Initially, ROT may be an identity matrix. The rotation elements of ROT may be determined by matrix multiplying the rotation elements specified by PresPh and the rotation elements specified by PastPh. Then, the following transformation operations are concatenated and applied to the model matrix of the one of objects 648 using a local 4×4 matrix T (which initially includes all 16 elements in the current model matrix: translate T to the negative of the center position of the one of objects 648 (−Center[x], −Center[y], −Center[z]) to eliminate interaction jitter; rotate T by ROT; translate T to the object center (Center[x], Center[y], Center[z]) to eliminate interaction jitter; and translate T to Delta Vector (DeltaVector[x], DeltaVector[y], DeltaVector[z]). Next, the model matrix is replaced with the T matrix.

Note that calculations related to the position of optional interaction tool 120 may occur every 15 ms or faster so that prehension related to optional interaction tool 120 is updated at least 66.67 times per second.

Moreover, tracking module 636 may track the head position of viewer 122 (FIG. 1), for example, using the one or more optional position sensors 116. Updates to head-position information 654 may be applied by graphics module 634 to the virtual space and used to render left-eye and right-eye images for display on display 114. Notably, the inverse of left-eye view matrix 656 may be revised by: translating the object relative to the position coordinate of the camera or the image sensor (the monoscopic view matrix $V_0$ that is located at the center of display 114); rotating by θ−90° (which specifies a normal to an inclined display); and translating to the eye of the viewer 122 in FIG. 1 by taking away the original offset d, translating to the current head position and translating left to 0.5ipd. Thus, $$V_{left\_eye}^{-1} = V_0^{-1} \cdot Rv(\theta - 90°) \cdot Tv(-d) \cdot Tv(\text{head\_position}) \cdot Tv\left(\frac{-ipd}{2}, 0, 0\right).$$

Similarly, left-eye frustum 658 may be revised by: translating to the current head position relative to the offset k (shown in FIGS. 3 and 4) between the eyes of viewer 122 in FIG. 1 and the viewing plane; and translating left to 0.5ipd. Thus, $$F_{left\_eye} = Tv(0, 0, k) \cdot Tv(\text{head\_position}) \cdot Tv\left(\frac{-ipd}{2}, 0, 0\right).$$

These operations may be repeated for the right eye to calculate right-eye view matrix 660 and right-eye frustum 662, i.e., $$V_{right\_eye}^{-1} = V_0^{-1} \cdot Rv(\theta - 90°) \cdot Tv(-d) \cdot Tv(\text{head\_position}) \cdot Tv\left(\frac{ipd}{2}, 0, 0\right).$$

and $$F_{right\_eye} = Tv(0, 0, k) \cdot Tv(\text{head\_position}) \cdot Tv\left(\frac{ipd}{2}, 0, 0\right).$$

Using the left-eye and the right-eye view and frustum matrices 656-662, graphics module 634 may determine left-eye image 664 for a given transformation model matrix Mt in model matrices 652 based at least in part on $Mt \cdot V_{left\_eye} \cdot F_{left\_eye}$, and may determine right-eye image 666 for the given transformation model matrix Mt based at least in part on $Mt \cdot V_{right\_eye} \cdot F_{right\_eye}$.

After applying monoscopic depth cues 668, graphics module 634 may display left-eye and right-eye images 666 and 668 on display 114. Note that calculations related to the head position may occur at least every 50-100 ms, and the rendered images may be displayed on display 114 at a frequency of at least 60 Hz for each eye.

In general, objects are presented in the rendered images on display 114 with image parallax. However, in an exemplary embodiment the object corresponding to optional interaction tool 120 on display 114 is not represented with image parallax.

Therefore computer system 600 may implement a datacentric approach (as opposed to a model-centric approach) to generate left-eye and right-eye images 664 and 666 with enhanced (or optimal) depth acuity for discrete-sampling data.

However, in other embodiments the imaging technique may be applied to continuous-valued or analog data. For example, data module 632 may interpolate between discrete samples in data 640. This interpolation (such as minimum bandwidth interpolation) may be used to resample data 640 and/or to generate continuous-valued data.

While the preceding discussion illustrated left-eye and right-eye frustums with near and far (clip) planes that can cause an object to drop out of left-eye and right-eye images 664 and 666 if viewer 122 (FIG. 1) moves far enough away from display 114, in some embodiments the left-eye and right-eye frustums provide a more graceful decay as viewer 122 (FIG. 1) moves away from display 114.

Furthermore, when the resulting depth acuity in left-eye and right-eye images 664 and 666 is sub-optimal, intuitive clues (such as by changing the color of the rendered images or by displaying an icon in the rendered images) may be used to alert viewer 122 (FIG. 1).

Furthermore, while the preceding embodiments illustrated prehension in the context of motion of optional interaction tool 120, in other embodiments additional sensory feedback may be provided to viewer 122 (FIG. 1) based at least in part on motion of optional interaction tool 120. For example, haptic feedback may be provided based at least in part on annotation, metadata or CT scan Hounsfield units about materials having different densities (such as different types of tissue) that may be generated by data module 632. This haptic feedback may be useful during surgical planning or a simulated virtual surgical procedure.

Because information in computer system 600 may be sensitive in nature, in some embodiments at least some of the data stored in memory 624 and/or at least some of the data communicated using communication module 628 is encrypted using encryption module 638.

Instructions in the various modules in memory 624 may be implemented in: a high-level procedural language, an object-oriented programming language, and/or in an assembly or machine language. Note that the programming language may be compiled or interpreted, e.g., configurable or configured, to be executed by the one or more processors 610.

Although computer system 600 is illustrated as having a number of discrete components, FIG. 6 is intended to be a functional description of the various features that may be present in computer system 600 rather than a structural schematic of the embodiments described herein. In some embodiments, some or all of the functionality of computer system 600 may be implemented in one or more application-specific integrated circuits (ASICs) and/or one or more digital signal processors (DSPs). Moreover, computer system 600 may be implemented using one or more computers at a common location or at one or more geographically distributed or remote locations. Thus, in some embodiments, computer system 600 is implemented using cloud-based computers. However, in other embodiments, computer system 600 is implemented using local computer resources.

Computer system 600, as well as electronic devices, computers and servers in graphical system 100 (FIG. 1), may include one of a variety of devices capable of performing operations on computer-readable data or communicating such data between two or more computing systems over a network, including: a desktop computer, a laptop computer, a tablet computer, a subnotebook/netbook, a supercomputer, a mainframe computer, a portable electronic device (such as a cellular telephone, a PDA, a smartwatch, etc.), a server, a portable computing device, a consumer-electronic device, a Picture Archiving and Communication System (PACS), and/or a client computer (in a client-server architecture). Moreover, communication interface 612 may communicate with other electronic devices via a network, such as: the Internet, World Wide Web (WWW), an intranet, a cellular-telephone network, LAN, WAN, MAN, or a combination of networks, or other technology enabling communication between computing systems.

Graphical system 100 (FIG. 1) and/or computer system 600 may include fewer components or additional components. Moreover, two or more components may be combined into a single component, and/or a position of one or more components may be changed. In some embodiments, the functionality of graphical system 100 (FIG. 1) and/or computer system 600 may be implemented more in hardware and less in software, or less in hardware and more in software, as is known in the art.

Methods

Figure 10:
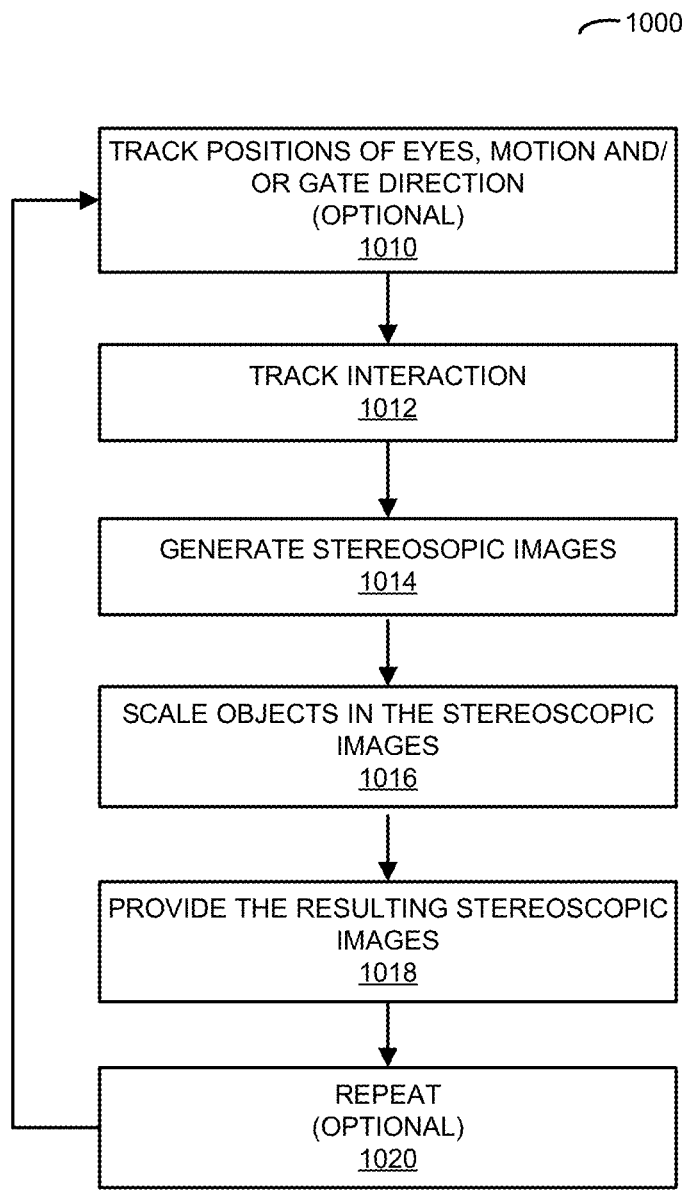
FIG. 10 is a flow diagram illustrating a method for providing stereoscopic images in accordance with an embodiment of the present disclosure.

FIG. 10 presents a flow diagram illustrating a method 1000 for providing stereoscopic images, which may be performed by graphical system 100 (FIG. 1) and, more generally, a computer system. During operation, the computer system generates the stereoscopic images (operation 1014) at a location corresponding to a viewing plane based at least in part on data having a discrete spatial resolution, where the stereoscopic images include image parallax. Then, the computer system scales objects in the stereoscopic images (operation 1016) so that depth acuity associated with the image parallax is increased, where the scaling (or stereopsis scaling) is based at least in part on the spatial resolution and a viewing geometry associated with a display. For example, the objects may be scaled prior to the start of rendering. Next, the computer system provides the resulting stereoscopic images (operation 1018) to the display. For example, the computer system may render and provide the stereoscopic images.

Note that the spatial resolution may be associated with a voxel size in the data, along a direction between images in the data and/or any direction of discrete sampling.

Moreover, the viewing plane may correspond to the display. In some embodiments, the computer system optionally tracks positions of eyes (operation 1010) of an individual that views the stereoscopic images on the display. The stereoscopic images may be generated based at least in part on the tracked positions of the eyes of the individual. Furthermore, the computer system may optionally track motion (operation 1010) of the individual, and may optionally re-generate the stereoscopic images based at least in part on the tracked motion of the individual (operation 1018) so that the stereoscopic images include motion parallax. Additionally, the computer system may optionally track interaction (operation 1012) of the individual with information in the displayed stereoscopic images, and may optionally re-generate the stereoscopic images based at least in part on the tracked interaction so that the stereoscopic images include prehension by optionally repeating (operation 1020) one or more operations in method 1000. For example, the individual may interact with the information using one or more interaction tools. Thus, when generating the stereoscopic images (operation 1014) or preparing the stereoscopic images, information from optionally tracked motion (operation 1010) and/or the optionally tracked interaction may be used to generate or revise the view and projection matrices.

Note that the stereoscopic images may include a first image to be viewed by a left eye of the individual and a second image to be viewed by a right eye of the individual. Moreover, the viewing geometry may include a distance from the display of the individual and/or a focal point of the individual.

In some embodiments, generating the stereoscopic images is based at least in part on: where the information in the stereoscopic images is located relative to the eyes of the individual that views the stereoscopic images on the display; and a first frustum for one of the eyes of the individual and a second frustum for another of the eyes of the individual that specify what the eyes of the individual observe when viewing the stereoscopic images on the display. Furthermore, generating the stereoscopic images may involve: adding monoscopic depth cues to the stereoscopic images; and rendering the stereoscopic images.

In some embodiments, the computer system optionally tracks a gaze direction (operation 1010) of the individual that views the stereoscopic images on the display. Moreover, an intensity of a given voxel in a given one of the stereoscopic images may be based at least in part on a transfer function that specifies a transparency of the given voxel and the gaze direction so that the stereoscopic images include foveated imaging.

Figure 11:
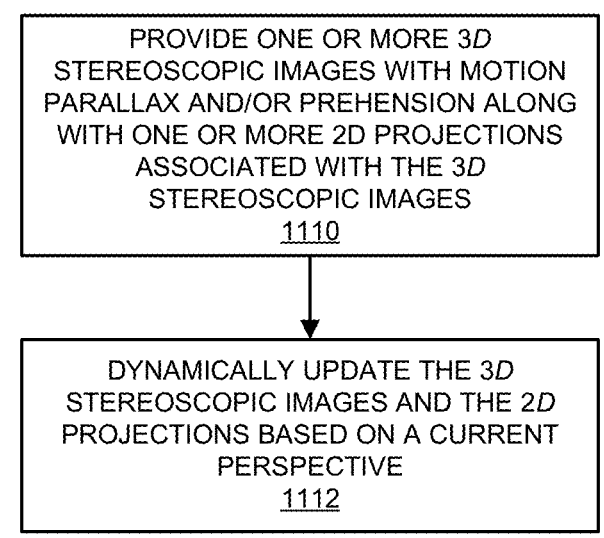
FIG. 11 is a flow diagram illustrating a method for providing 3D stereoscopic images and associated 2D projections in accordance with an embodiment of the present disclosure.

FIG. 11 presents a flow diagram illustrating a method 1100 for providing 3D stereoscopic images and associated 2D projections, which may be performed by graphical system 100 (FIG. 1) and, more generally, a computer system. During operation, the computer system provides one or more 3D stereoscopic images with motion parallax and/or prehension along with one or more 2D projections (or cross-sectional views) associated with the 3D stereoscopic images (operation 1110). The 3D stereoscopic images and the 2D projections may be displayed side by side on a common display. Moreover, as the user interacts with the 3D stereoscopic images and/or the one or more 2D projections and changes their viewing perspective, the computer system may dynamically update the 3D stereoscopic images and the 2D projections based at least in part on the current perspective (operation 1112). In some embodiments, note that the 2D projections are always presented along a perspective direction perpendicular to the user so that motion parallax is registered in the 2D projections.

In some embodiments of methods 1000 and/or 1100 there may be additional or fewer operations. Moreover, the order of the operations may be changed, and/or two or more operations may be combined into a single operation.

Applications

By combining image parallax, motion parallax, prehension and stereopsis scaling to create an interactive stereo display, it is possible for users of the graphical system to interact with displayed 3D objects as if they were real objects. For example, physicians can visually work with parts of the body in open 3D space. By incorporating the sensory cues associated with direct interaction with the displayed objects, it is believed that both cognitive and intuitive skills of the users will be improved. This is expected to provide a meaningful increase in the user's knowledge.

In the case of medicine, this cognitive-intuitive tie can provide a paradigm shift in the areas of diagnostics, surgical planning and a virtual surgical procedure by allowing physicians and medical professionals to focus their attention on solving clinical problems without the need to struggle through the interpretation of 3D anatomy using 2D views. This struggle, which is referred to as 'spatial cognition,' involves viewing 2D images and constructing a 3D recreation in your mind (a cognitively intensive process). In the absence of the True 3D provided by the graphical system, the risk is that clinically significant information may be lost. The True 3D provided by the graphical system may also address the different spatial cognitive abilities of the physicians and medical professionals when performing spatial cognition.

In the discussion that follows, an analysis technique that includes a 3D image of an LAA is used as an illustrative example of the application of the graphical system and True 3D. However, in other embodiments the graphical system and True 3D are used in a wide variety of applications, including medical applications (such as radiologic diagnosis and/or surgical navigation) and non-medical applications.

Figure 12:
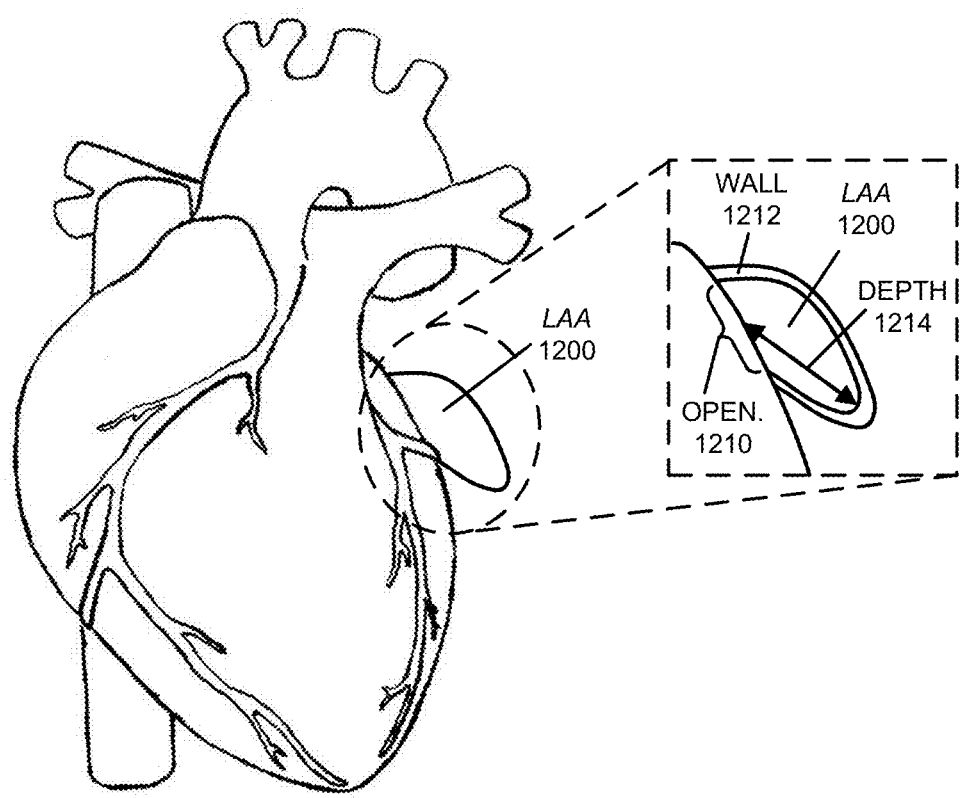
FIG. 12 is a drawing illustrating an LAA in accordance with an embodiment of the present disclosure.

As discussed previously, an LAA in conjunction with atrial fibrillation can result in serious medical consequences, such as a stroke. FIG. 12 presents a drawing illustrating an LAA 1200. This LAA, protrudes from the left atrium (thus, its name). As shown in the inset, which presents a cross-sectional view, LAA 1200 has an opening 1210 (defined by wall 1212 of LAA 1200) and a depth 1214. Moreover, opening 1210 has a cross-sectional area that varies along its length and depth 1214.

Typically, these and other anatomical features of an LAA are determined in advance using 2D TEE, and then 2D TEE and 2D fluoroscopy are used during a LAAC procedure to guide the insertion of a device that is used to close of the LAA. However, as discussed previously, 2D TEE usually provides limited anatomical understanding. For example, approximate anatomical dimensions are typically determined based at least in part on four different 2D TEE views or perspectives, and the results can vary based at least in part on user experience and the measurement technique. More generally, 2D projections of a 3D object (such as 2D TEE or fluoroscopy) are often difficult to interpret. All of which adds uncertainty to the device sizing, the surgical plan and procedure, which can make LAAC more challenging and can adversely impact patient outcomes. Thus, while 2D TEE and other non-invasive imaging techniques (such as fluoroscopy) can be convenient tools in many medical procedures, many challenges remain.

In order to address these problems, embodiments of an analysis technique that determines at least an anatomic feature associated with an LAA is described. Notably, using pre-operative CT data, True 3D may be used to present the relevant anatomy in its entirety. This approach may maintain the true spatial 3D anatomical relationships and, thus, may provide better and more-intuitive understanding of the LAA morphology. Moreover, this capability may allow a user to interact with the relevant anatomy in 3D and to use specific anatomical landmarks to automatically generate measurements of one or more anatomical features associated with an LAA.

Figure 13:
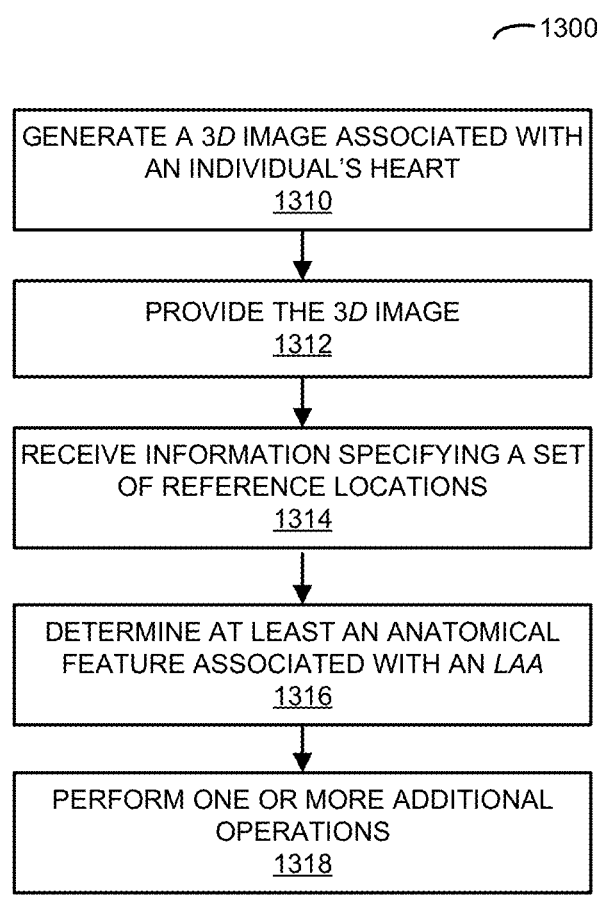
FIG. 13 is a flow diagram illustrating a method for determining at least an anatomic feature associated with an LAA in accordance with an embodiment of the present disclosure.

FIG. 13 presents a flow diagram illustrating a method 1300 for determining at least an anatomic feature associated with an LAA, which may be performed by graphical system 100 (FIG. 1) and, more generally, a computer or a computer system (such as computer system 600 in FIG. 6), which are used interchangeably in the present discussion.

During operation, the computer generates a 3D image (such as a 3D CT image) associated with an individual's heart (operation 1310). This 3D image may present a view along a perpendicular direction to an opening of the LAA. For example, the 3D image may provide an endoluminal view of the individual's anatomy relative to a 2D cut plane (which is sometimes referred to as a 'sectioning plane'). Notably, the computer may generate a stereoscopic or 3D image of at least a portion of the individual's heart based at least in part on a 3D model of the individual's body, such as a 3D image that was generated based at least in part on one or more 2D CT images using True 3D and the graphical system in FIGS. 1-7. Note that the 3D model (which is sometimes referred to as a 'reference model') may be determined by the computer based at least in part on one or more 2D CT images of the individual's body, such as one or more CT images. Thus, the 3D image may include at least a portion of the 3D volume data available for the individual. In some embodiments, after generating the 3D image, the computer optionally provides the 3D image (operation 1312), e.g., by displaying the 3D image on a display.

Note that the True 3D protocol may use virtual and augmented reality visualization systems that integrate stereoscopic rendering, stereoscopic acuity scaling, motion parallax and/or prehension capabilities to provide a rich holographic experience and a True 3D view of the individual. As described further below, these capabilities may provide spatial situational awareness that facilitates accurate assessment of the individual's anatomy.

Then, the computer may receive (or access in a computer-readable memory) information (operation 1314) specifying a set of reference locations. For example, the set of reference locations may include: a location on a circumflex artery, a location between a superior portion of the LAA and a left pulmonary vein (such as a tip of limbus), and a location on a superior wall of the LAA and distal to trabeculae carneae. Notably, the information specifying the set of reference locations may be received from a user of the computer. For example, the information may be received from an interaction tool and/or the information may correspond to haptic interaction between a digit of the user and a display. Thus, the user may specify or define the set of reference locations. Alternatively, the computer may determine the set of reference locations, which are subsequently accessed by the computer during method 1300.

Next, the computer automatically determines, based, at least in part, on the set of reference locations, at least the anatomical feature associated with the LAA (operation 1316), which is associated with the opening of the LAA and a size of a device used in an LAA closure (LAAC) procedure. The automatic measurements may be performed on the sectioning plane.

For example, the anatomical feature may include a volume, proximal and distal to a central cross-sectional area of the opening to the LAA along the perpendicular direction, in which the size of the device is unchanged. In some embodiments, the anatomical feature includes one or more of: the central cross-sectional area of the opening to the LAA, a wall thickness of the LAA, a diameter extremum of the central cross-sectional area of the opening, and/or a deepest depth of the device in the LAA.

Note that the automatic determination may involve determining cross-sectional areas of openings to the LAA at different distal locations toward an LAA satrium (or distal end), and confirming that the size of the device is unchanged at the different distal locations. In this way, the computer may determine a spatial margin for a given device size (such as based at least in part on a 3D size of the given device and an anatomical model of an LAA). In some embodiments, the computer receives (or accesses in a computer-readable memory) information specifying the central cross-sectional area of the opening to the LAA, and then the computer determined the cross-sectional areas of openings to the LAA at different proximal or distal locations relative to a location of the central cross-sectional area of the opening that defines a landing zone or spatial margins in which a particular device size can be deployed successfully.

In some embodiments, the computer system performs one or more optional additional operations (operation 1318). For example, the computer may determine the size of the device based, at least in part, on the determined anatomical feature, and may provide information specifying the determined device size (e.g., on a display, in an electronic or paper report, etc.). Notably, there may be a mapping or a look-up table between the anatomical feature(s) and the size of the device. However, in some embodiments the computer may receive (or may access in a computer-readable memory) the size of the device, e.g., from the user.

Moreover, the computer may use one or more determined anatomical features to create a simplified anatomical model of an LAA. This simplified anatomical model may include information associated with one or more dimensions of an LAA, such as: an ostium of the LAA, a landing zone, and/or a length or depth of the LAA (from the deepest point, as viewed along a line, to the ostium). Moreover, the location of the anatomical model relative to the septal crossing point may be specified. In some embodiments, the anatomical model includes information corresponding to one of more of: the volume, proximal and distal to the central cross-sectional area of the opening to the LAA along the perpendicular direction, the central cross-sectional area of the opening to the LAA, the wall thickness of the LAA, the diameter extremum of the central cross-sectional area of the opening, and/or the deepest depth of the device in the LAA. This simplified anatomical model may be presented or displayed in the context of the 3D image or volumetric view (such as in the 3D image) or, as described below, in the context of a simulated 2D fluoroscopy image (such as in the simulated 2D fluoroscopy image). This may allow the analysis technique to present visual information in real-time, such as during an LAA procedure, which may assist or be useful to a surgeon. For example, the 3D image and/or simulated 2D fluoroscopy image may be registered (such as using a local positioning system) to an echocardiogram, 2D TEE or C-arm fluoroscopy measurements, so that the displayed the 3D image and/or simulated 2D fluoroscopy image have immediate or actionable information for a surgeon.

Furthermore, the computer may compute a surgical plan for the LAAC procedure on the individual based, at least in part, on the size of the device, an associated predefined device model (which specifies the 3D size or geometry of the device), a landing zone for successful deployment of the device, a C-arm position and an actual or a simulated fluoroscope image, and/or a septal cross-section plan. For example, the surgical plan may include navigation of the device through the individual's body to the LAA (such as via a guide wire through the individual's circulatory system, through the septum, etc.) and an orientation of the device to occlude the LAA. In some embodiments, as part of the surgical planning, the computer may display one or more catheters, having different shapes, superimposed on the patient's anatomy to see which one fits best. Alternatively, the computer may analyze the predefined shapes of different catheters and the patient's anatomy (such as the cross-sectional area and shape of vessels, e.g., veins, in the patient's circulatory system) to select an appropriate catheter to recommend to the surgeon.

In some embodiments, the size of the device is determined using a model of the device (such as a geometric model). For example, the model of the device may include a finite element model that describes the compliance of the device to tissue. Note that the model of the device may be displayed in the 3D image (or volumetric view), the simulated 2D fluoroscopy image and/or a simulated enhanced 2D fluoroscopy image (such as a simulated enhancement associated with a contrast dye).

Alternatively or additionally, different models of the device may be imported or accessed, and graphical representations of the different models may be displayed in the 3D image, the simulated 2D image and/or the simulated 2D fluoroscopy image, so that a surgeon (or medical professional) can select a suitable or appropriate size of the aortic-valve device for use in a given LAA procedure. For example, the computer may select a model of the device for display based at least in part on one or more measured dimensions of an LAA.

Moreover, in some embodiments geometric parameters in the simplified anatomical model are stored in a computer-readable memory along with an identifier of a patient or an LAA procedure. In conjunction with stored information about an outcome and adverse event information, this stored information may be subsequently analyzed to determine modifications to the recommended device given the geometric parameters in the simplified anatomical model. In this way, past decisions and performance can be used to provide feedback that is used to update or revise the surgical plan for future LAA procedures in order to improve outcomes, reduce side effects or adverse events and/or to reduce treatment cost.

As noted previously, the fluoroscope image may include a simulated fluoroscope image. Moreover, CT measurements can be fused or viewed superimposed over a simulated fluoroscope image. Notably, the computer may generate a simulated 2D fluoroscopy image based at least in part on data in a predetermined 3D image (such as a 3D CT image) associated with an individual's body. Generating the simulated 2D fluoroscopy image may involve a forward projection, such as calculating accumulated absorption corresponding to density along lines, corresponding to X-ray trajectories, through pixels in the predetermined 3D image. Then, the computer may provide or display the simulated 2D fluoroscopy image with a 3D context associated with a predefined cut plane in the individual's body (e.g., the 3D context may be displayed superimposed on the simulated 2D fluoroscopy image). Note that the 3D context may include: a slice, based at least in part on a 3D model of the individual's body, having a thickness through the individual's body that includes the predefined cut plane; and/or a stereoscopic image of at least a portion of the individual's body based at least in part on the 3D model of the individual's body. Alternatively or additionally, the 3D context may include at least partial views of anatomical structures located behind the predefined cut plane. Furthermore, based at least in part on the 3D model, the computer may provide another stereoscopic image adjacent to the simulated 2D fluoroscopy image with the 3D context. The other stereoscopic image may specify relative positions of a fluoroscopy source in a C-arm measurement system, a detector in the C-arm measurement system and the predefined cut plane, which may allow the displayed information to be intuitively viewed in context. Additionally, an orientation of the predefined cut plane may be specified based at least in part on: a position of a fluoroscopy source and a detector in a C-arm measurement system; and/or a received user-interface command associated with user-interface activity. In some embodiments, the simulated 2D fluoroscopy image includes simulated enhancement that gives the appearance of having a contrast dye injected from the catheter to further highlight the relevant LAA anatomy. (Notably, the desired anatomy may be segmented out of a first fluoroscopy image and a second fluoroscopy image may be created using this region as a mask and with the desired enhancement. Then, the two fluoroscopy images may be combined or merged, to produce a simulated fluoroscopy image with at least a portion that includes the simulated enhancement or artificially inflated values for the anatomy that is of interest.) Note that a user (such as a surgeon) may toggle or change the displayed information between the simulated 2D fluoroscopy image and the simulated enhanced 2D fluoroscopy image via a user interface (such as by activating a physical or a virtual icon, using a spoken command, etc.). For example, the user may toggle or change the displayed information to simulate the injection of a contrast dye if there is a structure of interest, such as in order to make an outline of the left atrium or an LAA darker, or to highlight the relative position of the catheter. Alternatively of additionally, the user interface may be used to present one of multiple modes, by continuously blending the simulated 2D fluoroscopy image and the simulated enhanced 2D fluoroscopy image with different relative weights. The ability to adjust the simulated contrast dye may be analogous to the ability of a surgeon or clinician to modify the concentration of their contrast dye.

In some embodiments, method 1300 may automatically generate the 3D image along the perpendicular direction (operation 1310), automatically receive the information (operation 1314) and/or automatically determine the anatomical feature associated with the LAA (operation 1316). However, in some embodiments, method 1300 may employ haptic annotation. Notably, the computer may provide, on a display, a 3D image (such as a stereoscopic image) of a portion of an individual (such as a cross section of a volume or a multiplanar-reconstruction image), where the 3D image has an initial position and orientation. Then, the computer may receive information (such as from a user interface) specifying a 2D plane in the 3D image, where the 2D plane has an arbitrary angular position relative to the initial orientation (such as at an oblique angle relative to a symmetry axis of the individual). The 2D plane may be positioned at a zero-parallax position so that 3D information in the 2D plane is perceived as 2D information. Moreover, the computer may translate and rotate the 3D image so that the 2D plane is presented on a reference 2D plane of the display with an orientation parallel to the reference 2D plane (so that the normal to the 2D plane is parallel to the normal of the reference 2D plane). Note that, prior to the translating and the rotating, the angular position may be different than that of the reference 2D plane and may be different from a predefined orientation of slices in the 3D image. Next, the computer may receive information specifying the detailed annotation in the 2D plane (such as information corresponding to haptic interaction between a digit of a user and the display), where the detailed annotation includes: a size of the anatomical structure based at least in part on annotation markers, an orientation of the anatomical structure, a direction of the anatomical structure and/or a location of the anatomical structure. After the annotation is complete (such as when after the computer receives a command indicating that the annotation is complete), the computer may translate and rotate the 3D image back to the initial position and orientation. Separately or in addition to the preceding operations, in some embodiments the computer may assist a surgeon with other aspects of surgical planning and/or during a surgical procedure. Notably, the computer may automatically perform one or more measurements of an ostium or opening in an LAA, each of which may be perpendicular to the deepest visible point in the LAA (such as the deepest point that can be reached along a linear path from the ostium of the LAA, which is sometimes referred to as a 'depth' of the LAA) and one or more coordinates of a septal cross-section plan (e.g., where the septum is to be punctured with a catheter and crossed in a surgical plan). Moreover, the computer may determine a route or path for how to navigate from the septum crossing to the ostium of the LAA. Alternatively or additionally, during a surgical procedure, in a first mode, the model of the device may be registered to a patient's anatomy using, e.g., ultrasound (such as an echocardiogram or 2D TEE). Then, the model may be displayed, in real time, at the appropriate dynamic position and superimposed on or independently of the actual device in a 3D image and/or a simulated 2D fluoroscopy image. Moreover, landmarks may be displayed to assist the surgeon in the surgical procedure. Furthermore, in a second mode, the model may be removed from the 3D image and/or the simulated 2D fluoroscopy image.

Note that the depth of an LAA may be calculated by the computer relative to the plane or landing zone where the device will land in the surgical procedure. For example, based at least on the landing zone, the computer may calculate the diameter or a centroid of the oval shaped ostium of the LAA. Then, the computer may use ray tracing in a cone centered on or emanating from the centroid of the ostium of the LAA to search for the deepest point of the LAA along a line from the landing zone. By determining the depth of the LAA, the analysis technique may help ensure that the that the appendage is long enough and deep enough to contain the entire implantation device. Alternatively, if the appendage is not long enough to support the device, implantation will not be successful.

While the preceding example illustrated an embodiment in which a single anatomic structure is annotated, in other embodiments the preceding operations are repeated one or more times to facilitate accurate determination of detailed multi-point annotation of an anatomical structure. For example, a 3D image of a portion of an individual may be iteratively transformed. Notably, for a given marker point, in response to receiving information specifying a 2D plane having an arbitrary angular position in the 3D image, the 3D image may be translated and rotated from an initial position and orientation so that the 2D plane is presented in an orientation parallel to a reference 2D plane of a display. Then, after annotation information specifying the detailed annotation in the 2D plane of the given marker point is received, the 3D image may be translated and rotated back to the initial position and orientation. These operations may be repeated for one or more other marker points.

In some embodiments of method 1300 there may be additional or fewer operations. Moreover, the order of the operations may be changed, and/or two or more operations may be combined into a single operation.

We now described exemplary embodiments of the analysis technique. Before an interventionalist (such as a surgeon or an invasive cardiologist) can implant the device, they may need to first obtain access to the left atrium of the heart. Part of this process is the septal cross, in which the doctor enters the right atrium of the heart through the inferior vena cava, and then has to push a catheter through the cardiac wall or septum separating the right atrium and the left atrium.

The analysis technique may assist the surgeon with this part of the procedure. Notably, as described further below with reference to FIGS. 15 and 16, the analysis technique may be used to define or determine the landing zone of the device, which indicates the desired location for implantation. The landing zone may specify a plane at the ostium of the LAA that shows how the surgeon wants the device to be oriented in the appendage.

Furthermore, the analysis technique may then allow the surgeon to highlight the fossa ovalis (which is the thinnest section of the septum between the right and left atria, and is where the implanter wants to make the septal cross). Next, the analysis technique may visual indicate the relationship between the fossa ovalis and the ostium of the LAA.

Figure 14:
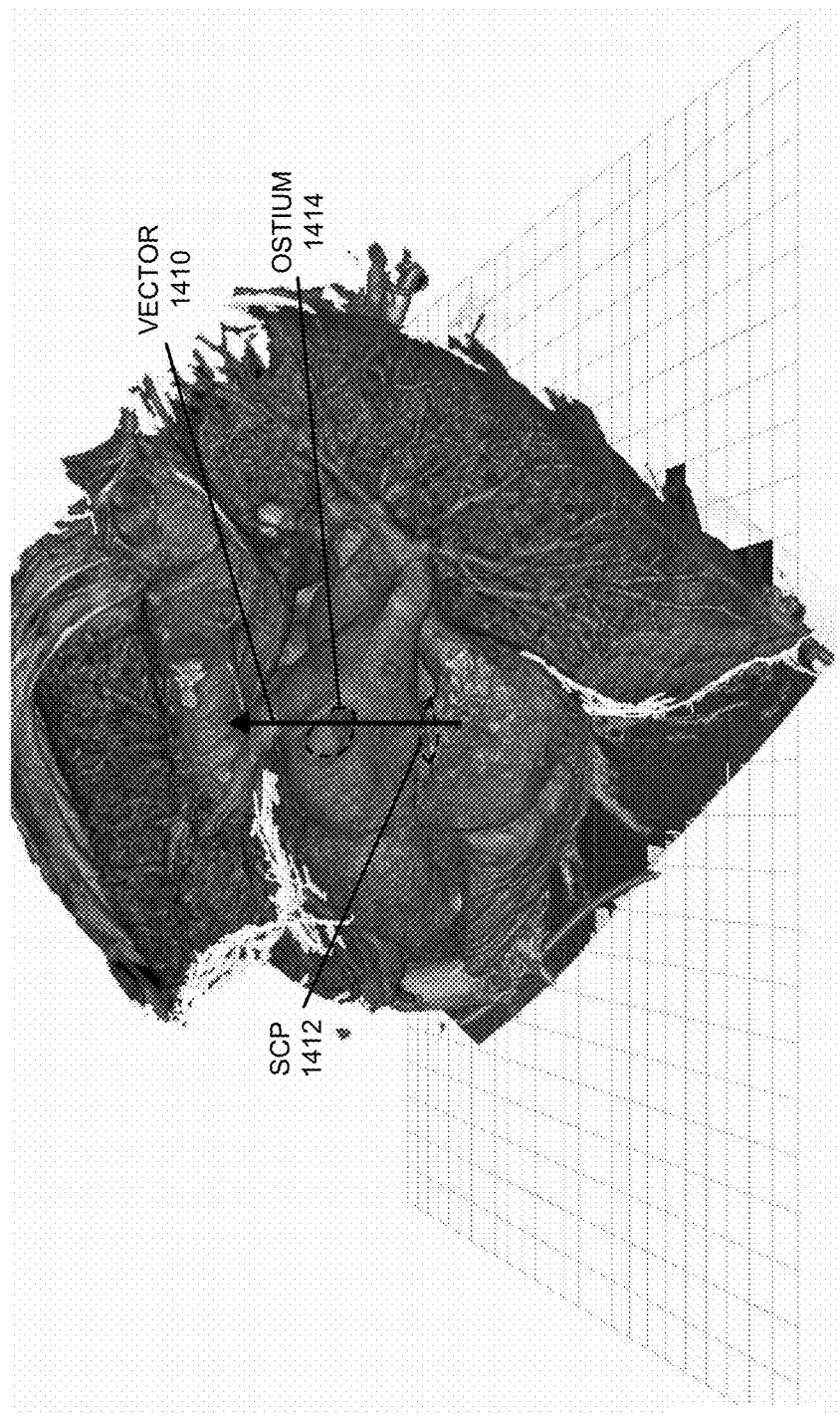
FIG. 14 is a drawing illustrating a septal cross-section plan in accordance with an embodiment of the present disclosure.

FIG. 14 presents a drawing illustrating a septal cross-section plan. This image includes a vector 1410 from the septal crossing point (SCP) 1412 to the ostium 1414 of the LAA. This may give a surgeon an indication of where to puncture the septum with a catheter and how to move or navigate to the ostium of the LAA. In some embodiments, a user may use the computer to outline or indicate the fossa ovalis in the image of the heart (which may correspond to a thinnest portion of the septal wall), which may be indicated in the image. This visual information may allow the surgeon to see the direction of the catheter through the septal wall during the surgical procedure.

Thus, the vector may from a centroid of the ostium of the LAA (and which is normal to the ostium plane) to the fossa ovalis (and, in particular, which is normal to the plane of the fossa ovalis). This vector may show the trajectories that the catheter may need to take in order to achieve the desired implantation location.

Alternatively or additionally, because the shapes and sizes of the delivery catheters are known, the analysis technique may calculate, based at least in part on the plane of the ostium of the LAA, which of the shapes is best suited to traverse the space between the fossa ovalis and the ostium. Moreover, the displayed image(s) may be used to visualize a 3D object in the shape(s) of these one or more catheters to further illustrate the path that the interventionalist will try to follow during a surgical procedure. Furthermore, the analysis technique may determine the shape of delivery catheter that would work best given that the interventionalist punctures through the fossa ovalis at a specific location. In these embodiments, the displayed image(s) may be colored or shaded in the areas of the fossa ovalis that correspond to one or more particular delivery catheters.

Figure 15:
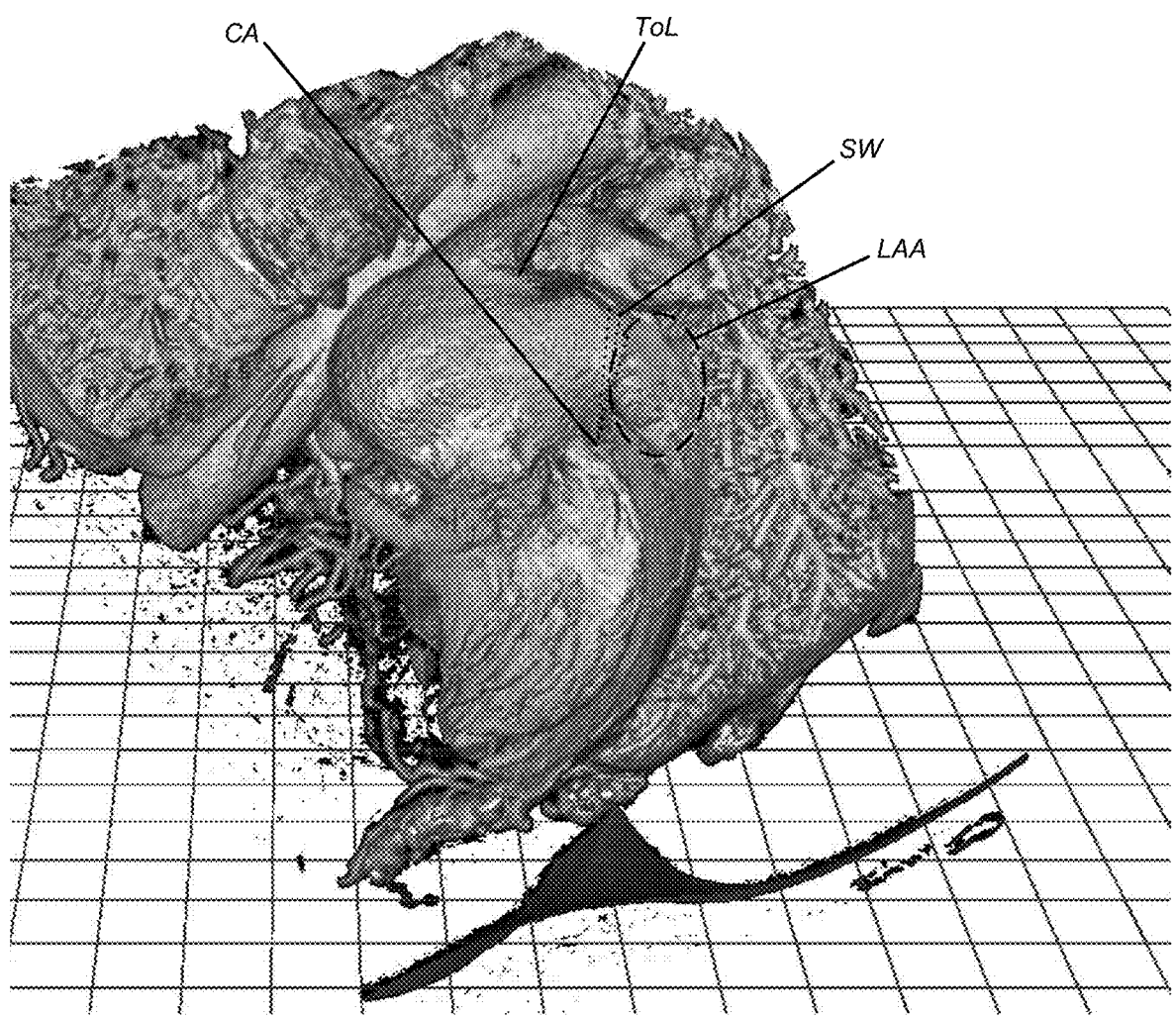
FIG. 15 is a drawing illustrating a workflow for determining at least an anatomic feature associated with an LAA in accordance with an embodiment of the present disclosure.
Figure 16:
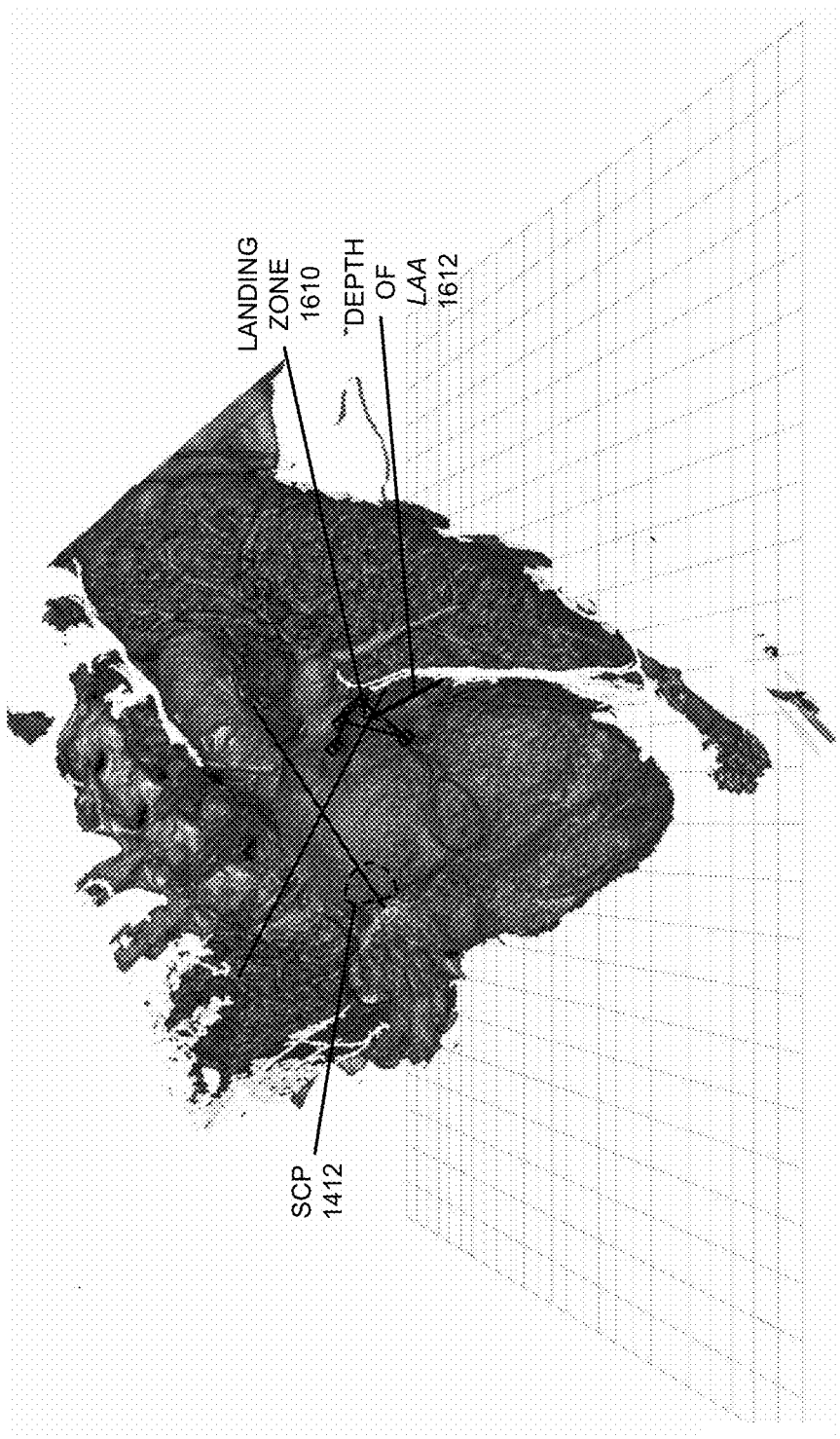
FIG. 16 is a drawing illustrating a landing zone for an LAA in accordance with an embodiment of the present disclosure.

As noted previously, the analysis technique may be used to determine one or more anatomical features associated with an LAA and to determine or define a landing zone for the device used to close the LAA. This is shown in FIG. 15, which presents a drawing illustrating a workflow for determining at least an anatomic feature associated with an LAA, and FIG. 16 presents a drawing illustrating a landing zone for an LAA. Referring to FIG. 15, a computer may orient the data in a 3D profile view of the LAA. For example, the computer may provide a 3D image with an endoluminal view of the LAA and the surrounding anatomy relative to a sectioning plane. More generally, the computer may provide a 3D image a long a direction perpendicular to a plane of the LAA based at least in part on 2D CT images. This 3D image may include anatomy anterior and superior to the LAA.

Then, a user may provide information that specifies the set of reference locations. For example, the user may mark: the location of the circumflex artery (CA); the location of the tip of the limbus or ToL (and, more generally, a location between superior part of LAA and the left pulmonary vein); and/or a point on the superior wall (SW) of the LAA, e.g., just past the trabeculae carneae. Note that the trabeculae carneae (which are sometimes referred to as 'columnae carneae' or 'meaty ridges') are rounded or irregular muscular columns that project from the inner surface of the right and left ventricles of the heart. Thus, the set of references locations may be manually specified. However, in other embodiments, the computer may determine some or all of the set of reference locations, e.g., using an image-analysis technique, a neural network, etc. Note that the image-analysis technique may extract features from the 2D CT images and/or the 3D image, such as: edges associated with objects, corners associated with the objects, lines associated with objects, conic shapes associated with objects, color regions within the image, and/or texture associated with objects. In some embodiments, the features are extracted using a description technique, such as: scale invariant feature transform (SIFT), speed-up robust features (SURF), a binary descriptor (such as ORB), binary robust invariant scalable keypoints (BRISK), fast retinal keypoint (FREAK), and/or another image-analysis technique.

Using the set of reference locations, the computer may automatically determine one or more anatomical features associated with the LAA. For example, the computer may determine a central measurement of the cross-sectional area of a plane at an opening of or entrance to the LAA. (However, in other embodiments, the user may provide information specifying this cross-sectional area.) This central measurement may be considered 'ideal,' and the user and/or the computer may determine the device size based, at least in part, on this value. For example, the device size may be determined based, at least in part, on a mapping of a look-up table that relates one or more anatomical features of an LAA, such as the cross-sectional area of the central measurement and/or and, as described below, a size of a landing zone, uncertainty in one or more of the anatomical features (e.g., a depth of the LAA) and/or a spatial margin associated with a given size of the device). As shown in FIG. 6, in some embodiments, a size of landing zone 1610 may be 13.95 mm in diameter, and a depth of the LAA 1612 may be 29.03 mm at 35° from a normal to landing zone 1610.

Then, the computer may perform proximal and distal measurements (relative to the central measurement) to determine a 'landing zone' in which the size of the device is the same. For example, the computer may increment the location along a direction perpendicular to the central opening and towards the LAA stratium, and may confirm that the size of the device is unchanged. In this way, the computer may determine the landing zone for a 27.87-mm device. In FIG. 15, the central measurement of the opening and the landing zone proximal and distal from this opening are illustrated by the dashed lines.

Note that central cross-sectional area and the proximal and distal distances in the landing zone along the perpendicular direction may define a volume, which is indicative of a spatial margin for the device size. Alternatively or additionally, the spatial margin in a perpendicular direction to the plane of the central measurement may be determined based at least in part on the size of the device. For example, the spatial margin may be determined based, at least in part, on the deepest point a device can go into the LAA (from the plane of the central measurement into the LAA).

One or more other measurements that may be performed by the computer may include: an outline of the wall of the LAA on the central cross-sectional area, a minimum diameter of the cross-sectional area (on the central measurement or in the landing zone), and/or a maximum diameter of the cross-sectional area (on the central measurement or in the landing zone).

In some embodiments, the computer may use the size of the device, an associated model of the device (such as a geometric model) and/or the measured anatomical features to determine at least a portion of a surgical plan. For example, the computer may determine an orientation of the device in the LAA and/or a path of a guide wire to/from the LAA.

Thus, the analysis technique may reduce or eliminate the time needed to orient the plane of the central measurement and to determine the one or more anatomical features associated with the LAA.

In some embodiments, the user may selectively instruct or define parameters used by the computer when determining the anatomical feature(s) associated with an LAA. For example, the user may selectively modify parameters that, in part, specify how the computer determines the anatomical feature(s) using a user interface. FIG. 17 presents a drawing illustrating a user interface 1700. Notably, a search box (proximal and distal) to the central measurement that is used to bound the spatial search/determination of the landing zone. Moreover, instead of a volume, the landing zone may be specified by a wedge. Using user interface 1700, the user may rotate the wedge proximally or distally from the central measurement plane. Furthermore, using user interface 1700, the user can specify visualization options, such as setting the view orientation or perspective and/or setting a visibility of the measurement. Based at least in part on the specified parameters, the computer may automatically update the one or more determined anatomical features shown in user interface 1700.

By determining the anatomical feature associated with the LAA, this analysis technique may facilitate anatomical situation awareness by the user (and, more generally, improved anatomic understanding). For example, the analysis technique may facilitate: more accurate sizing of a device used in a LAAC procedure, improved surgical planning for the LAAC procedure, and/or more accurate placement of the device. Consequently, the analysis technique may speed up the LAAC procedure, may reduce the complexity of the LAAC procedure and/or may improve patient outcomes for the LAAC procedure.

While the preceding embodiments used CT images and LAA to illustrate the analysis technique, the analysis technique may be used with other types of data, including data associated with different medical modalities and applications, as well as non-medical applications.

Figure 18:
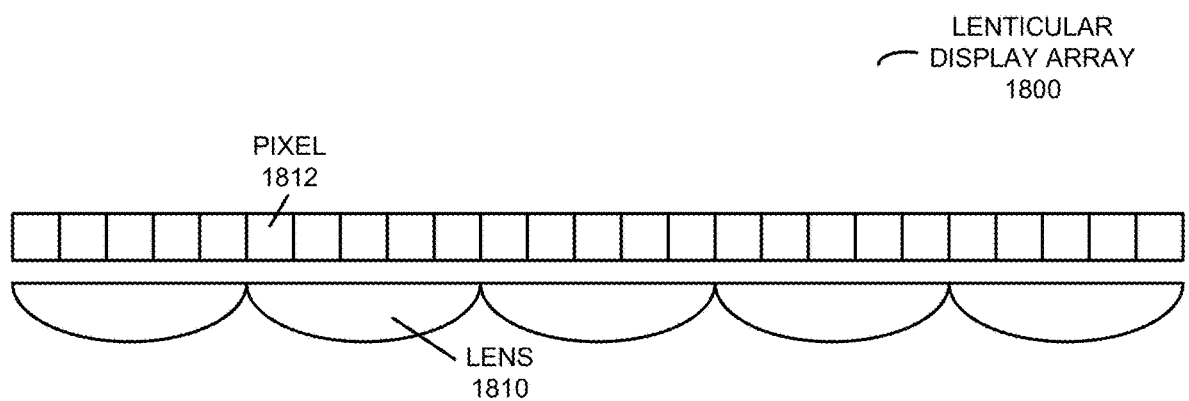
FIG. 18 is a drawing illustrating a side view of a lenticular array display in accordance with an embodiment of the present disclosure.

When the preceding embodiments are used in conjunction with a lenticular array display or a parallax-barrier-type display, the computer system may perform so-called 'pixel mapping' or 'dynamic subpixel layout' (DSL). This is illustrated in FIG. 18, which presents a drawing illustrating a side view of a lenticular array display 1800. As described further below with reference to FIGS. 19-23, when generating stereoscopic images, the computer system may position a current rendered image in pixels (such as pixel 1812) in an LCD panel on the display, so that the optics sends or directs the current rendered image to an eye of interest (such as the left or right eye). The pixel mapping may be facilitated by a combination of head or gaze tracking, knowledge of the display geometry and mixing of the current rendered image on a subpixel level (such as for each color in an RGB color space). For example, the current rendered image may be displayed in pixels corresponding to the left eye 60% of the time and in pixels corresponding to the right eye 40%. This pixel-based duty-cycle weighting may be repeated for each color in the RGB color space. Note that the duty-cycle weighting may be determined by the position of which ever eye (left of right) that is closest to the optical mapping of a display lens (such as lens 1810) and the current rendered image. In some embodiments, a left or right projection matrix is used to define how the rays from the current rendered image relate to a tracked left or right eye. Thus, based at least in part on the position of the left and right eyes relative to lenticular array display 1800, the computer system may give more duty-cycle weighting to the left eye or the right eye.

In some embodiments, during the pixel mapping, the computer system dynamically drives pixels (via RGB buffers), so that the views correspond to the positions of the left and right eyes of an individual. Notably, there may be separate buffers for the left-eye and right-eye views, and each of these buggers may be an RGB buffer. Therefore, with a single RGB buffer, there may be different integrations or duty-cycle weightings for the RGB images for the left and right eyes corresponding to the left-eye and right-eye views. This integration or mixing provides the appropriate combination of the left-eye and the right-eye views to improve or optimize the light received by an individual's eyes. Note that this approach may provide more of a continuous adjustment, which can improve the performance.

In some embodiments, the duty-cycle weight or integration is not perfect. Consequently, in order to avoid crosstalk, the computer system may apply the pixel mapping to those pixels that need mixed intensity, and may not apply the pixel mapping to the remainder of the pixels (such as those in a black background, in order to obtain the correct color). Thus, there may be a binary decision as to whether or not to apply the pixel mapping to a given pixel.

Alternatively or additionally, in some embodiments a phase shift is applied to the drive pixels based at least in part on the left and right eye positions or locations. Note that this approach may be more discrete, which may impact the overall performance.

We now further describe DSL. Autostereoscopic, plenoptic or light filed displays are multiview 3D displays that can be seen without glasses by the user. They provide a potential opportunity to overcome the discomfort caused by wearing 3D stereoscopic glasses or head mounted displays. This may be useful in use cases where the additional eye/head-ware is a physical limitation, such as in the medical field where maintaining sterility of the operating field of a surgery is important.

Existing autostereoscopic displays often provide directionality to pixels by inserting an optical layer such as a lenticular lens or a parallax barrier between a flat LCD panel and the user. However, this approach often has limitations, which are mainly because of the decrease in resolution and narrow viewing zones. Notably, the optical layer between the light source and the viewer transforms the spatial distribution of the pixels into a spatio-angular distribution of the light rays. Consequently, the resolution of the 3D images is typically reduced by the number of viewpoints. Moreover, the decrease in resolution is also related with expressing a large depth of field. Usually, multiview displays suffer from poor depth of field. For example, an object that is at a distance from the display panel may become blurry as the depth increases, and more viewpoints are needed for crisp image expression. Furthermore, the viewing range of a multiview display is often limited to a predefined region at the optimal viewing distance or OVD (which is sometimes referred to as 'the sweet spot'), and dead zones can occur between the sweet spots, where the disparity of the stereo image is inverted and a pseudoscopic 3D image appears.

Figure 19:
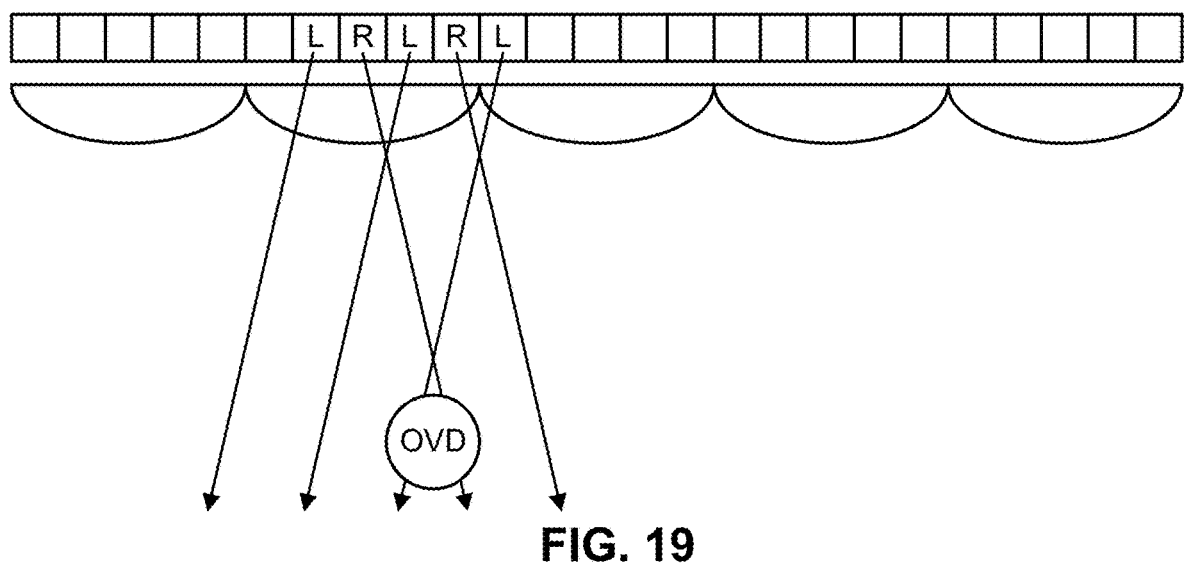
FIG. 19 is a drawing illustrating a side view of operation of the lenticular array display of FIG. 18 in accordance with an embodiment of the present disclosure.

However, adding head or eye-tracking to such displays may enable the user to view the 3D content with continuous motion parallax and with sufficient depth range. This is shown in FIG. 19, which presents a drawing illustrating a side view of operation of lenticular array display 1800. Note that the head or eye-tracking approach may allow the viewer's head and/or eyes to be tracked, and may use the position information to optimize the pixel resources (as described previously).

In some embodiments, the DSL technique is used to implement an eye-tracking-based autostereoscopic 3D display. This technique may match the optical layer (e.g., the lenticular lens) parameters to subpixel layouts of the left and right images to utilize the limited pixel resources of a flat panel display and to provide stereoscopic parallax and motion parallax. Because light rays are close to the optical axis of the lens, Snell's Law may be used to estimate the light ray direction.

Figure 20:
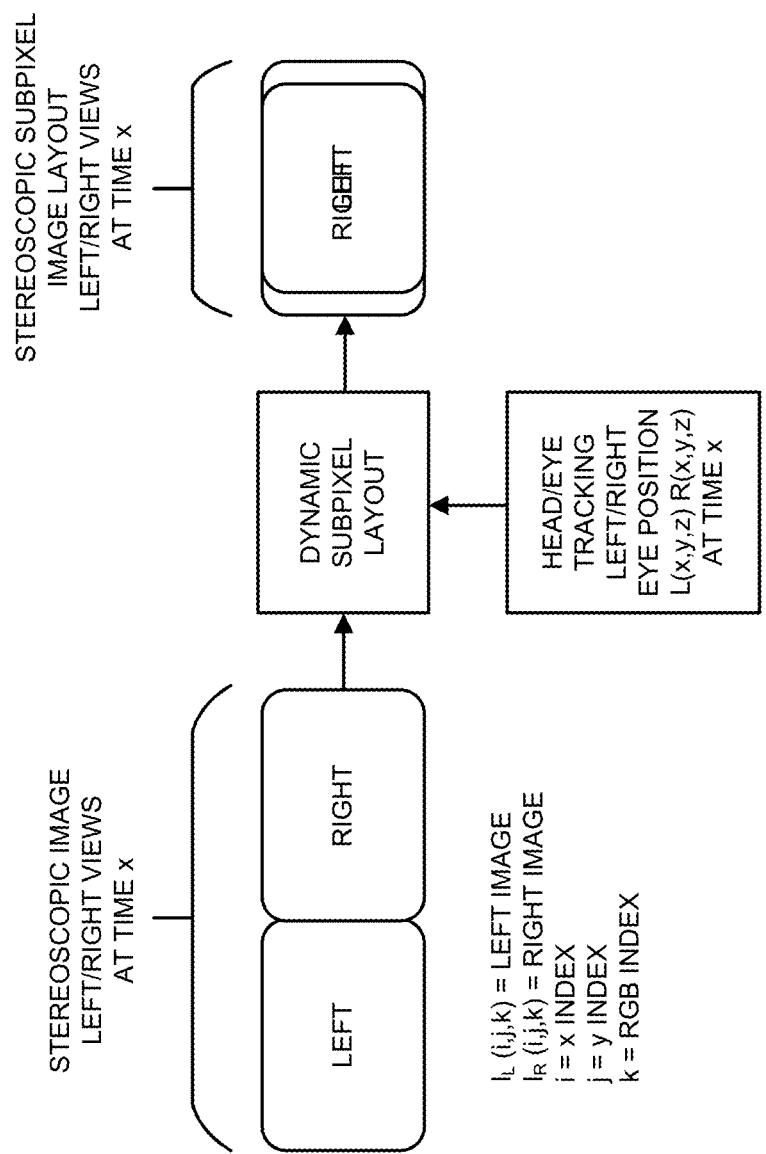
FIG. 20 is a drawing illustrating operation of the lenticular array display of FIG. 18 in accordance with an embodiment of the present disclosure.

The process in the DSL technique is shown in FIG. 20, which presents a drawing illustrating operation of lenticular array display 1800 (FIG. 18). The inputs in the DSL technique may be a stereo image pair (left and right images), the display and lens parameters, and the 3D head or eye positions of the user or viewer. Note that the image parameters may include $I_L(I,j,k)$ and $I_R(I,j,k)$, where i and j are the x and y index pixels and the k index is an RGB subpixel value that may directly map to the LCD panel subpixels. For example, red may equal 0, green may equal 1 and blue may equal 2.

Figure 21:
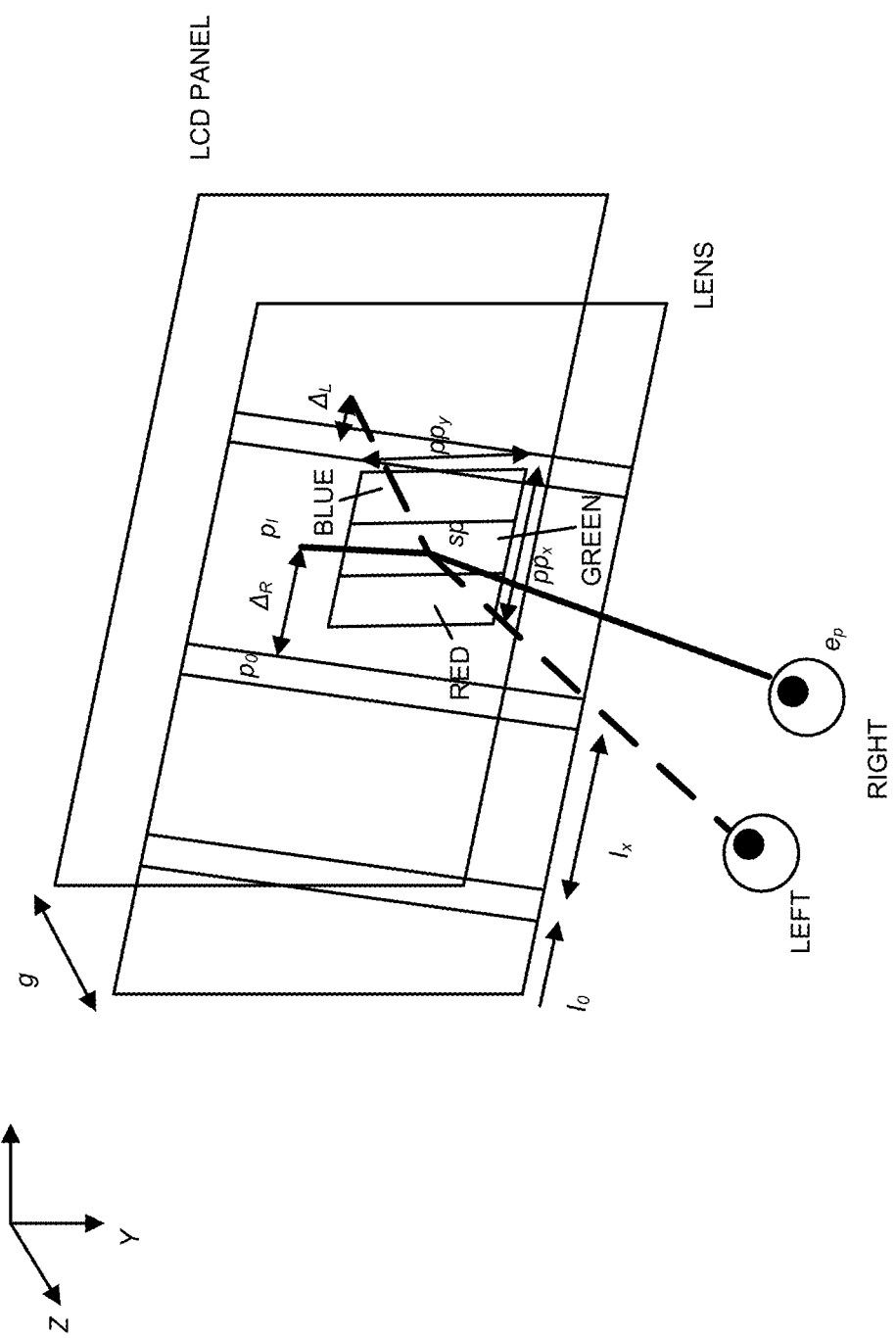
FIG. 21 is a drawing illustrating a front view of the lenticular array display of FIG. 18 in accordance with an embodiment of the present disclosure.

Moreover, as shown in FIG. 21, which presents a drawing illustrating a front view of lenticular array display 1800, the display parameters may include a lens slanted angle ($\theta$), a lens pitch in x ($l_x$), a lens start position ($l_0$), and a gap (g) distance between the lens and the LCD panel. Furthermore, the lens start position may denote the horizontal distance from the display coordinate origin to the center of the first lenticular lens. Additionally, the 3D eye positions ($e_p$), which may be obtained by a head or eye tracker (e.g., in terms of the camera coordinates), may be transformed to display coordinates. Notably, ep may equal ($x_{ep}$, $y_{ep}$, $z_{ep}$), the eye position in x, y, z.

In the DSL technique, the 'layout' may be controlled by defining at the subpixel level (e.g., the RGB elements) a weighted left or right-view dominant component. The resulting image may be a combination of left and right pixels dynamically arranged to a single image that contains both left and right image information matched to the lens.

By estimating how light rays emanate from the eye of the viewer or user and pass through the lens and onto the LCD panel, each subpixel may be assigned to use the image subpixel value of its corresponding left or right image. Moreover, the subpixel may be generated at the center of the lens on the same horizontal plane.

Figure 22:
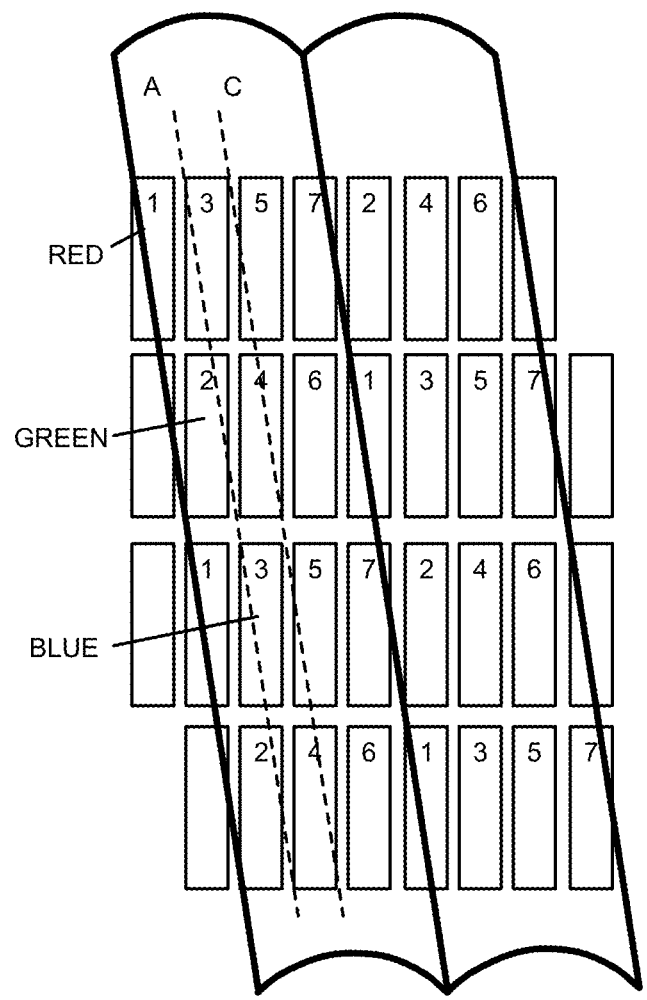
FIG. 22 is a drawing illustrating a viewing geometry of the lenticular array display of FIG. 18 in accordance with an embodiment of the present disclosure.

For example, as shown in FIG. 22, which presents a drawing illustrating a viewing geometry of lenticular array display 1800 (FIG. 18), the lens may be on a slant and may contain N views (such as 7 views). Two perspectives may render a left and right view. Each of the views may be 'laid out' so as to match the optics of the lens and tracked position of the user (per the render). The 'layout' may be controlled by defining at the subpixel level (e.g., the RGB elements) a weighted left or right-view dominant component. The resulting image may be a dynamically arranged combination of left and right pixels.

Notably, in FIG. 22, the ray direction close to the position of the user or viewer may be traced using the display parameters, and it may be compare with the ray directions from the RGB subpixel to the left and right eye positions. In some embodiments, the 3D light refraction at the surface of glass, which may be caused by the difference in the refraction indices of glass and air (via Snell's law), may be considered in the ray-tracing estimation. In FIG. 22, note that: ppx, ppy may be the pixel pitch in x, y; lr may be the refractive index of a lens; $\Delta$ may be a distance from a projected eye position to the lens opening (one for left and right eye); sp may be a subpixel; $p_1$ may be the ($x_{p1}$, $y_{ep}$, $z_{ep}$) lens projection of the eye position(s) on an LCD panel; and $p_0$ may be the ($xp_0$, $yp_0$, $zp_0$) position of a closest lens in the horizontal direction.

Note that the x, y positions of a current subpixel sp ($x_{sp}$, $y_{sp}$, k) may be expressed as $$x_{sp} = ipp_x + \frac{(k+0.5)pp_x}{3}, \text{ and}$$

$$y_{sp} = jpp_y + 0.5pp_y.$$

Then, the computer system may calculate pix, the position of the corresponding position of the eye position $e_p$ ($x_{ep}$, $y_{ep}$, $z_{ep}$) through the lens at the LCD panel plane, which are connected via the current subpixel position sp by 3D ray tracing model.

Considering the refractive index of air equal to 1, Snell's law can be expressed as $$\frac{\sin\left(\tan^{-1}\frac{r_l}{g}\right)}{\sin\left(\tan^{-1}\frac{r_{ep}}{z_{ep}}\right)} = \frac{1}{lr},$$

where g is the gap distance between the lens and the LCD panel, lr is the refractive index of the lens, $e_p$ ($x_{ep}$, $y_{ep}$, $z_{ep}$) is the eye position x, y, z, $r_1$ is a ray of light from the lens to the LCD panel, and $r_e$ is a ray of light from the eye position $e_p$ to the lens.

Thus, with the refractive index of air equal to 1, $r_l = \sqrt{\|x_{pl} - x_{sp}\| + \|y_{pl} - y_{sp}\|}$ and $r_e = \sqrt{\|x_{ep} - x_{sp}\| + \|y_{ep} - y_{sp}\|}.$ Then, $$r_l = g\tan\left(\sin^{-1}\frac{\sin\left(\tan^{-1}\frac{r_e}{z_e}\right)}{lr}\right).$$

This gives $$x_{pl} = x_{sp} + \frac{r_e}{r_l}(x_{ep} - x_{sp}),$$

with $x_{p0}$, the x position of the closest lens in the horizontal direction $$x_{p0} = \text{round}\left(\frac{x_{pl} - l_0}{l_x}\right)l_x + l_0 \text{ and } l_0 = l_x - \frac{r_l}{r_e}(y_{ep} - y_{pl})\tan\theta,$$

where $l_0$ is the sum of the lens start position and the lens position offset by the subpixel $y_{sp}$ and lens $y_{pl}$ difference. The distance from the projected eye position to the lens is $\Delta = |x_1 - x_0|.$ By comparing the distances from the projected left/right eye positions to the lens lenticules, the pixel value or subpixel (considering the k index) value may be determined as the left image or right image as $I(I,j,k) = I_L(i,j,k) \text{ if } \Delta_L < \Delta_R$, or $I_R(i,j,k)$ otherwise.

Figure 23:
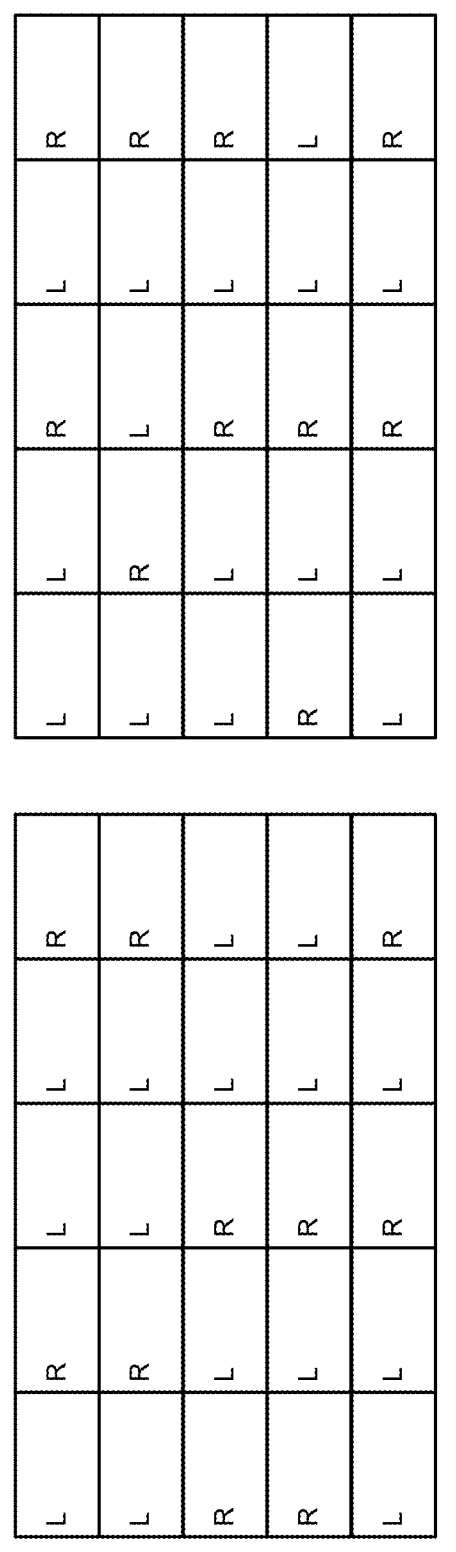

FIG. 23 presents a drawing illustrating dynamic mapping of pixels to tracked eye positions of a viewer. Note that the left mapping table shows view 1 at time 1, and contains the left and right perspective views. Moreover, the right mapping table shows view 2 and time 2, and contains the left and right perspective views.

While the preceding examples use specific numerical values, these are illustrations of the analysis technique and are not intended to be limiting. In other embodiments, different numerical values may be used.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for providing determining at least an anatomic feature of a left atrial appendage (LAA), comprising: by a computer:
   generating a three-dimensional (3D) image associated with an individual's heart, wherein the 3D image presents a view along a perpendicular direction to an opening of the LAA;
   receiving information specifying a set of predefined anatomical reference locations, wherein the set of predefined anatomical reference locations comprise: a location on a circumflex artery, a location between a superior portion of the LAA and a left pulmonary vein, and a location on a superior wall of the LAA and distal to trabeculae carneae; and
   automatically determining, based, at least in part, on the set of predefined anatomical reference locations, at least the anatomical feature of the LAA, wherein the anatomical feature is associated with the opening of the LAA and a fixed size of a device used in an LAA closure (LAAC) procedure.

2. The method of claim 1, wherein the 3D image provides an endoluminal view of the individual's anatomy relative to a two-dimensional (2D) sectioning plane.

3. The method of claim 1, wherein the anatomical feature includes a volume, proximal and distal to a central cross-sectional area of the opening to the LAA along the perpendicular direction, in which the fixed size of the device is unchanged.

4. The method of claim 1, wherein the anatomical feature includes one or more of: a central cross-sectional area of the opening to the LAA, a wall thickness of the LAA, a diameter extremum of the central cross-sectional area of the opening, or a deepest depth of the device in the LAA.

5. The method of claim 1, wherein the automatic determination may involve determining cross-sectional areas of openings to the LAA at different distal locations toward an LAA satrium, and confirming that the fixed size of the device is unchanged at the different distal locations.

6. The method of claim 1, wherein the method comprises:
   selecting the fixed size of the device based, at least in part, on the determined anatomical feature; and
   providing information specifying the determined fixed size of the device.

7. The method of claim 1, wherein the method comprises computing a surgical plan for the LAAC procedure on the individual based, at least in part, on the fixed size of the device and an associated predefined device geometrical model.

8. The method of claim 7, wherein the surgical plan includes navigation of the device to the LAA and an orientation of the device to occlude the LAA.

9. The method of claim 1, wherein the information is one of: associated with an interaction tool; or corresponds to haptic interaction with a display.

10. A non-transitory computer-readable storage medium for use in conjunction with a computer, the computer-readable storage medium storing a program that facilitates determining of at least an anatomic feature of a left atrial appendage (LAA), wherein, when executed by the computer, the program module causes the computer to perform one or more operations comprising:
    generating a three-dimensional (3D) image associated with an individual's heart, wherein the 3D image presents a view along a perpendicular direction to an opening of the LAA;
    receiving information specifying a set of predefined anatomical reference locations, wherein the set of predefined anatomical reference locations comprise: a location on a circumflex artery, a location between a superior portion of the LAA and a left pulmonary vein, and a location on a superior wall of the LAA and distal to trabeculae carneae; and
    automatically determining, based, at least in part, on the set of predefined anatomical reference locations, at least the anatomical feature of the LAA, wherein the anatomical feature is associated with the opening of the LAA and a fixed size of a device used in an LAA closure (LAAC) procedure.

11. The computer-readable storage medium of claim 10, wherein the 3D image provides an endoluminal view of the individual's anatomy relative to a two-dimensional (2D) sectioning plane.

12. The computer-readable storage medium of claim 10, wherein the anatomical feature includes a volume, proximal and distal to a central cross-sectional area of the opening to the LAA along the perpendicular direction, in which the fixed size of the device is unchanged.

13. The computer-readable storage medium of claim 10, wherein the anatomical feature includes one or more of: a central cross-sectional area of the opening to the LAA, a wall thickness of the LAA, a diameter extremum of the central cross-sectional area of the opening, or a deepest depth of the device in the LAA.

14. The computer-readable storage medium of claim 10, wherein the automatic determination may involve determining cross-sectional areas of openings to the LAA at different distal locations toward an LAA satrium, and confirming that the fixed size of the device is unchanged at the different distal locations.

15. The computer-readable storage medium of claim 10, wherein the one or more operations comprise:
    selecting the size of the device based, at least in part, on the determined anatomical feature; and
    providing information specifying the determined fixed size of the device.

16. The computer-readable storage medium of claim 10, wherein the one or more operations comprises computing a surgical plan for the LAAC procedure on the individual based, at least in part, on the fixed size of the device and an associated predefined device geometrical model.

17. The computer-readable storage medium of claim 16, wherein the surgical plan includes navigation of the device to the LAA and an orientation of the device to cap the LAA.

18. A computer, comprising:
    a processor; and
    memory, coupled to the processor, which stores a program module, wherein, when executed by the processor, the program module causes the computer to perform one or more operations comprising:
        generating a three-dimensional (3D) image associated with an individual's heart, wherein the 3D image presents a view along a perpendicular direction to an opening of the LAA;
        receiving information specifying a set of predefined anatomical reference locations, wherein the set of predefined anatomical reference locations comprise: a location on a circumflex artery, a location between a superior portion of the LAA and a left pulmonary vein, and a location on a superior wall of the LAA and distal to trabeculae carneae; and
        automatically determining, based, at least in part, on the set of predefined anatomical reference locations, at least the anatomical feature of the LAA, wherein the anatomical feature is associated with the opening of the LAA and a fixed size of a device used in an LAA closure (LAAC) procedure.

19. The computer of claim 18, wherein the operations comprise:
    selecting the size of the device based, at least in part, on the determined anatomical feature; and
    providing information specifying the determined fixed size of the device.

20. The computer of claim 18, wherein the operations comprise computing a surgical plan for the LAAC procedure on the individual based, at least in part, on the fixed size of the device and an associated predefined device geometrical model.

* * * * *